United States Patent
Labib et al.

(10) Patent No.: US 6,857,436 B2
(45) Date of Patent: *Feb. 22, 2005

(54) METHOD OF CLEANING PASSAGEWAYS USING A MIXED PHASE FLOW OF A GAS AND A LIQUID

(75) Inventors: Mohamed Emam Labib, Princeton, NJ (US); Ching-Yue Lai, Lawrenceville, NJ (US); Peter A. Materna, Metuchen, NJ (US); Geoffrey Lawrence Mahon, Ridgewood, NJ (US)

(73) Assignee: Princeton Trade & Technology, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/197,287

(22) Filed: Jul. 16, 2002

(65) Prior Publication Data

US 2002/0189647 A1 Dec. 19, 2002

Related U.S. Application Data

(60) Division of application No. 09/466,714, filed on Dec. 17, 1999, now Pat. No. 6,454,871, and a continuation-in-part of application No. 08/880,662, filed on Jun. 23, 1997, now Pat. No. 6,027,572.

(51) Int. Cl.$^7$ .................................................. B08B 7/04
(52) U.S. Cl. ................ 134/22.1; 134/22.11; 134/22.12; 134/22.18; 134/22.19; 134/37
(58) Field of Search ........................... 134/22.1, 22.11, 134/22.12, 22.18, 34, 37

(56) References Cited

U.S. PATENT DOCUMENTS

| | | | |
|---|---|---|---|
| 2,222,516 A | 11/1940 | Powell et al. | 134/22.12 |
| 3,625,231 A | 12/1971 | Littrell et al. | 134/102 |

(List continued on next page.)

FOREIGN PATENT DOCUMENTS

| | | | |
|---|---|---|---|
| DE | 893595 | 10/1953 | |
| EP | 490117 A1 | 6/1992 | B08B/9/06 |
| EP | 634229 B1 | 10/1998 | B08B/9/06 |
| SU | 1042826 A | 9/1983 | B08B/9/02 |

OTHER PUBLICATIONS

Hobbe et al., "Use of Nucleopore Filters for Counting Bacteria by Fluoescence Microscopy", Appl. and Environ Microbiol. vol. 33, No. 5, May 1977, pp 1226–1228.

Kogure et al, "A tentative directr microscopic method for counting living marine bacteria", Can. J. Microbiol. vol. 25, 1979, pp415–420.

(List continued on next page.)

Primary Examiner—Michael Barr
Assistant Examiner—Saeed Chaudhry
(74) Attorney, Agent, or Firm—Merchant & Gould P.C.

(57) ABSTRACT

A method of cleaning surfaces using a mixed phase cleaning mixture of an aqueous solution and a flow of gas sufficient to produce droplets of the liquid which are entrained by the gas for a time sufficient to clean tubing of various lengths and geometries and porous membranes to remove biofilm, debris and contaminants.

48 Claims, 5 Drawing Sheets

U.S. PATENT DOCUMENTS

| | | | |
|---|---|---|---|
| 3,811,408 A | 5/1974 | Thompson | 118/73 |
| 4,169,123 A | 9/1979 | Moore et al. | 422/28 |
| 4,219,333 A | 8/1980 | Harris | 8/137 |
| 4,222,346 A | 9/1980 | Reisgies | 119/14.18 |
| 4,311,618 A | 1/1982 | Schafer-Burkhard | 252/542 |
| 4,380,477 A | 4/1983 | Saunders | 134/7 |
| 4,444,597 A | 4/1984 | Gortz et al. | 134/18 |
| 4,477,438 A | 10/1984 | Willcockson et al. | 424/130 |
| 4,517,081 A | 5/1985 | Amiot et al. | 210/321.6 |
| 4,525,220 A | 6/1985 | Sasa et al. | 134/22.18 |
| 4,695,385 A | 9/1987 | Boag | 210/636 |
| 4,710,233 A | 12/1987 | Hohmann et al. | 134/1 |
| 4,744,951 A | 5/1988 | Cummings et al. | 422/28 |
| 4,776,794 A | 10/1988 | Meller | 433/216 |
| 4,863,688 A | 9/1989 | Schmidt et al. | 422/28 |
| 4,874,002 A | 10/1989 | Sundholm | 134/111 |
| 4,881,563 A | 11/1989 | Christian | |
| 4,902,352 A | 2/1990 | Christian | |
| 4,988,485 A | 1/1991 | Bene | 422/292 |
| 5,007,461 A | 4/1991 | Naf | 134/22.12 |
| 5,045,352 A | 9/1991 | Mueller | 134/22.12 |
| 5,077,008 A | 12/1991 | Kralovic | 422/37 |
| 5,107,875 A | 4/1992 | Sundholm | 134/99 |
| 5,159,956 A | 11/1992 | Kurihara | 137/624.13 |
| 5,160,548 A | 11/1992 | Boisture | 134/7 |
| 5,197,499 A | 3/1993 | Bodenmiller et al. | 134/95.2 |
| 5,244,468 A | 9/1993 | Harris et al. | 8/137 |
| 5,286,301 A | 2/1994 | Albrecht | 134/8 |
| 5,287,867 A | 2/1994 | Plummer et al. | 134/56 |
| 5,344,652 A | 9/1994 | Hall, II et al. | 424/495 |
| 5,395,456 A | 3/1995 | Abrams et al. | 134/22.14 |
| 5,408,991 A | 4/1995 | Iida et al. | 128/4 |
| 5,423,917 A | 6/1995 | Garcia, Jr. | 134/1 |
| 5,425,815 A | 6/1995 | Parker et al. | 134/26 |
| 5,445,761 A | 8/1995 | Shah et al. | 252/94 |
| 5,462,605 A | 10/1995 | Szucs | 134/7 |
| 5,480,565 A | 1/1996 | Levin et al. | 210/764 |
| 5,494,530 A | 2/1996 | Graf | 134/22.12 |
| 5,529,788 A | 6/1996 | De Senna | 424/466 |
| 5,589,507 A | 12/1996 | Hall, II et al. | 514/557 |
| 5,595,344 A | 1/1997 | Starnes | 239/307 |
| 5,615,695 A | 4/1997 | Chambers | 134/102.1 |
| 5,616,616 A | 4/1997 | Hall, II et al. | 514/557 |
| 5,628,959 A | 5/1997 | Kross | 134/27 |
| 5,635,195 A | 6/1997 | Hall, II et al. | 424/405 |
| 5,651,893 A | 7/1997 | Kenley et al. | 210/636 |
| 5,656,302 A | 8/1997 | Cosentino et al. | 424/616 |
| 5,674,323 A | 10/1997 | Garcia | |
| 5,698,100 A | 12/1997 | Levin et al. | 210/321.6 |
| 5,699,817 A | 12/1997 | Bankert et al. | 134/102.2 |
| 5,714,060 A | 2/1998 | Kenley et al. | 210/194 |
| 5,723,090 A | 3/1998 | Beerstecher et al. | 422/26 |
| 5,731,275 A | 3/1998 | Prevost et al. | 510/261 |
| 5,795,404 A | 8/1998 | Murphy et al. | 134/22.18 |
| 5,837,204 A | 11/1998 | Prevost et al. | 422/105 |
| 5,840,343 A | 11/1998 | Hall, II et al. | 424/616 |
| 5,858,114 A | 1/1999 | Board et al. | 134/18 |
| 5,961,937 A | 10/1999 | Gobbato | 422/300 |
| 6,019,117 A | 2/2000 | Detsch et al. | 137/15 |
| 6,027,572 A * | 2/2000 | Labib et al. | 134/8 |
| 6,142,170 A | 11/2000 | Belfer et al. | 137/246 |
| 6,207,201 B1 | 3/2001 | Piacenza | 424/665 |
| 6,261,457 B1 | 7/2001 | Wenthold et al. | 210/636 |
| 6,326,340 B1 | 12/2001 | Labib et al. | 510/161 |
| 6,423,152 B1 | 7/2002 | Landaas | 134/10 |
| 6,454,871 B1 * | 9/2002 | Labib et al. | 134/8 |

OTHER PUBLICATIONS

Azzopardi, B., "Drops in annular two–phase flow," *Int. J. Multiphase Flow*, vol. 23, Suppl., pp. 1–53 (1997).

Barajas, A. et al., "The effects of contact angle on two phase flow in capillary tubes," *Int. J. Multiphase Flow*, vol. 19, No. 2, pp. 337–346 (1993).

Henstock, W. et al., "The Interfactial Drag and the Height of the Wall Layer in Annular Flows," *AlChE Journal*, vol. 22, No. 6, pp. 990–999 (Nov. 1976).

Hewitt, G. et al., "Annular Two–Phase Flow," *Pergamon Press*, pp. v–vii, 1–20, chapters 1–2 (Date Unknown).

Klauer, J., "Piping: An examination of pipe self cleaning in high–purity water systems," *Ultrapure Water*, pp. 56–60 (Mar. 2001).

Reinemann, D., "Dairy operators guide to milking machine cleaning and sanitation," *Paper written for presnetation at the NRAES the Milking Systems and Parlors Conference*, 8 pages (Jan. 30, 2001).

Riedewald, F., "Biofilms in Pharmaceutical Waters," *Pharmaceutical Engineering*, 8 pages (Nov./Dec. 1997).

Tragardh, C., "Cleaning in air–water–flow," *Division of Food Engineering, Land Engineering, Alnarp (Sweden)*, pp. 424–429 (Date Unknown).

Triplett, K. et al., "Gas liquid two–phase flow in microchannels. Part 1: two–phase flow patterns," *International Journal of Multiphase Flow*, vol. 25, pp. 377–380, 387–393 (1999).

Woodmansee, D. et al., "Mechanism for the removal of droplets from a liquid surface by a parallel air flow," *Chemical Engineering Science*, vol. 24, pp. 299–307 (1969).

* cited by examiner

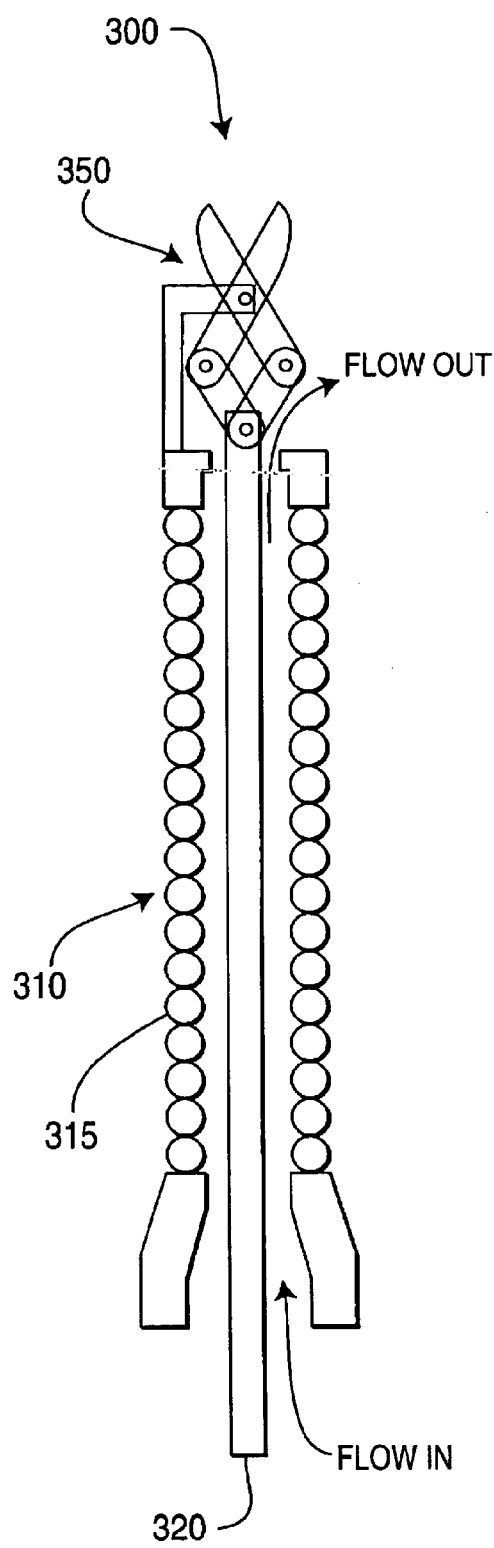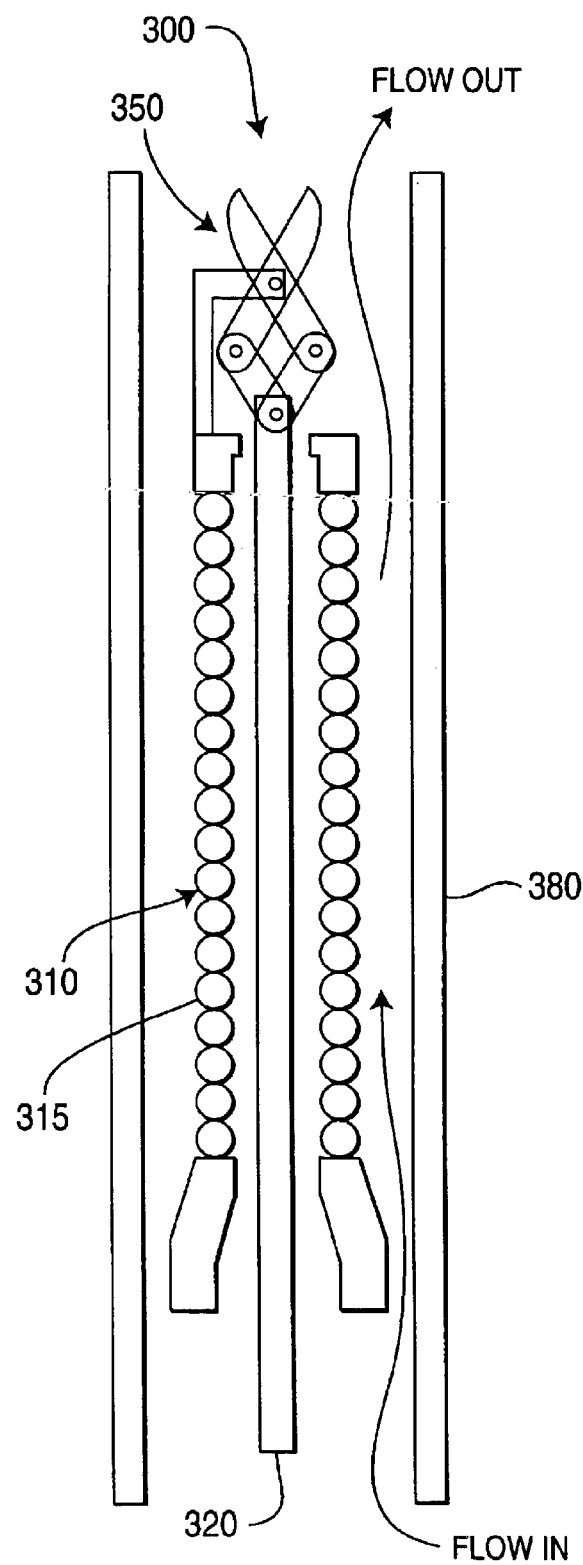
FIG. 3A
FIG. 3B

METHOD OF CLEANING PASSAGEWAYS USING A MIXED PHASE FLOW OF A GAS AND A LIQUID

This application is a divisional of U.S. application Ser. No. 09/466,714 that was filed with the United States Patent and Trademark Office on Dec. 17, 1999, and that issued as U.S. Pat. No. 6,454,871 on Sep. 24, 2002. U.S. application Ser. No. 09/466,714 is a continuation-in-part of U.S. application Ser. No. 08/880,662 that was filed with the United States Patent and Trademark Office on Jun. 23, 1997, and issued as U,S. Pat. No. 6,027,572 on Feb. 22, 2000. The entire disclosures of U.S. application Ser. No. 09/466,714 and U.S. application Ser. No. 08/880,662 are incorporated herein by reference.

This invention relates to a method for removing biofilm, debris, contaminants and the like from the surfaces of passageways, including passageways which have irregular or complex shapes or whose walls are permeable, using a mixed-phase cleaning solution.

BACKGROUND OF THE INVENTION

Interior surfaces of passageways such as small-bore tubing, pipes, ducts and the like, which may carry fluids such as liquids, gases, slurries or aerosols, are very difficult to clean and to maintain in a clean condition. When the flow path is long and narrow, or hard to reach, it is difficult to clean the surfaces by conventional liquid phase flushing because such a long, narrow passageway limits liquid flow velocities by creating a high resistance to flow. As a result, shear stresses which could aid in the removal of contaminants from such surfaces are limited. Low flow velocities also limit the usefulness of solvents for the same reasons.

Cleaning of small diameter passageways is also difficult because of the nature of certain types of residues. Fluid passageways which supply water, even purified water, develop bacterial and fungal growth from the water on their interior surfaces, as is well known. Bacteria present in the water strongly adhere to tubing surfaces and then grow laterally, forming what is known as biofilm. Biofilm is apparent to the touch as a slimy film and is composed of both organic residues and the multiplying microorganisms. The bacteria deposit an underlying structural matrix comprising polysaccharides with some peptide moieties, calcium carbonate and other materials which adhere to the surfaces of the passageways. An illustrative example is dental unit water line tubing, which carries rinse water to the mouth of a dental patient. It has been determined that, in the absence of any special precautions, this water exiting from such tubing can include as much as one million ($1 \times 10^6$) colony-forming units of bacteria per milliliter of water (CFU/ml). The source has been shown to be the surface biofilm which sheds bacteria into the flowing water. The American Dental Association has recommended reduction of the level of bacteria present in dental water delivery systems to below 200 CFU/ml to be adopted by the year 2000. Thus, these water lines and tubing must be periodically disinfected or cleaned to ensure the deactivation of viable bacteria and the removal of this biofilm from the walls of the tubing in order to prevent infection in dental patients. Removal of biofilm from passageways is also necessary for other applications, including medical, industrial and food service applications, because such biofilms are the main cause of high bacterial counts and high levels of endotoxins.

However, removing biofilm from fluid passageways is quite difficult, which makes disinfecting the surface more difficult as well. The biofilm is strongly adherent to passageway surfaces, whether the surface is made from natural materials, such as rubber or metals, or synthetic polymeric materials, such as polyvinylchloride, polyethylene, polytetrafluoroethylene and the like. Treatment with chemical agents, such as disinfectant and biocidal agents, can kill the exposed surface bacteria and so reduce the contribution of the biofilm to the total bacterial count. However, these agents do not readily diffuse into the entire thickness of the biofilm. The biofilm protects the remaining viable bacteria which then rapidly multiply. If it happens that all of the bacteria are killed, the biofilm structure remains an ideal host for new bacteria to colonize and grow. Thus these treatments are generally only partially effective, and the original levels of viable bacteria return quite rapidly. In order to remove biofilm from a surface, in addition to chemical treatment, some mechanical action is necessary to produce shear stress or sufficient impact at the surface.

In dentistry, there are applications for cleaning and disinfecting both tubing and the dental handpiece. The handpiece, which contains an air-driven turbine or other method of driving a drill and other parts, is about six inches long and is detachable. The tubing and other passageways inside the handpiece have a ratio of length to inside diameter of about 100. At present the most common sterilization procedure is steam autoclaving. However, in addition to the fact that autoclaving does not actually remove debris from the handpiece, this autoclaving procedure can be damaging to the turbine and various seals in the handpiece. For example, the operating rotational speed of a dental drill has been found to decrease with the number of sterilizations performed.

The old method of cleaning dental handpieces is to flush them with water or a cleaning solution. While this may flush non-adherent biofilm and debris from passageways, it can be shown that it provides little or no removal of adherent biofilm and debris such as blood, mucous and the like. In order to obtain more force behind the liquid flushing, Littrell, U.S. Pat. No. 3,625,231, describes a device utilizing compressed air to force a quantity of a cleaning and conditioning fluid through the passageways of the handpiece. This device primarily uses single-phase liquid flow as evidenced by the requirement to observe the clarity of the fluid being expelled from the handpiece as a criterion for cleaning. This method is only slightly more effective than flushing with water but may be significantly better than flushing with a hand-operated syringe. However, complete removal of adherent biofilm, debris and contaminants will not occur.

Cleaning of instruments, handpieces and the like by spraying with water or cleaning solutions is also well known. The spray may be generated by an aerosol can or an atomizing device. While this is a useful method of distributing a cleaning solution, it does not ensure complete cleaning of adherent debris. Complete cleaning only occurs when the adhesion of the debris is overcome by shear stress. Additionally, an effective cleaning method may act to weaken the adhesive bond between the debris and the surface to which it adheres to reduce the required stress. The adhesive strength must be overcome by a significant margin to ensure complete cleaning. Total coverage of all surfaces by shear stress is required and sufficient mass transfer must be provided to prevent loosened debris from shielding unloosened debris. Simple spraying does not ensure that these conditions are met.

It can be estimated that prior art techniques which use a total of only a drop or two of liquid would not provide enough liquid for the surface area of a dental handpiece tube to achieve significant re-formation of droplets. One or two drops equals tenths of a milliliter. The present method uses a continuous flow for a period of time such that the amount of liquid used for the same purpose would be tens of milliliters, some two orders of magnitude higher.

In addition to biofilm, passageways of various medical devices may contain food particles, particles of various bodily tissues, mucous, saliva, unclotted or clotted blood or blood components, pathogens, macromolecules and the like, which are referred to hereinafter as "debris". It is also necessary to remove this debris from the passageways in which it exists. Such debris may even need to be cleaned from passageways which are not fluid-carrying passageways in the normal use of the device, such as where a cable slides inside a sheath or conduit in an endoscope or biopsy device. Infections arising from the use of endoscopic devices have been reported and traced to the inefficient cleaning and debris removal by conventional methods.

Endoscopes may contain a passageway for use of a biopsy device, as well as passageways for other purposes. Both the internal passageways and the exterior of the endoscope must be cleaned after each use. The biopsy device itself also has interior and exterior surfaces which must be kept clean. Guidelines for cleaning gastrointestinal and other flexible endoscopy units promulgated by the American Society for Gastrointestinal Endoscopy and other bodies include a multi-step method for cleaning tubing between uses to prevent cross-infection between patients. First, mechanical cleaning using a brush and a detergent solution is performed soon after use. The tubing is then rinsed with water and then a disinfection is carried out using a liquid chemical disinfectant such as as a gluteraldehyde solution. The tubing is then rinsed with sterile water and dried with forced air. However, this method is time-consuming and suffers from inefficiency in removing all pathogens and other debris, as well as being subject to variations in technique from one operator to another.

In devices such as heat exchangers, there is a need to remove biofilm, algae, mineral deposits or corrosion products, the last two being referred to as scale, from their surfaces. Such substances decrease the thermal efficiency of heat exchangers.

There are also applications for the cleaning of fluid passageways whose walls are permeable. Surfaces which are permeable or porous are frequently described as membranes. Herein, the term membrane is used to denote porosity and permeability for a surface of any geometry, and most commonly a geometry which is of a tubular shape or other shape more complex than flat, such as a hollow fiber filter or a hemodialyzer or a spiral wound filter. Applications in which the wall of the fluid passageway is a permeable membrane include microfiltration, ultrafiltration, kidney dialysis, reverse osmosis and the like. In such applications it is necessary to remove from the membrane such contaminants as small particles of any undesirable substances, large molecular weight macromolecules, biofilm, and (in the case of hemodialyzers) adsorbed serum proteins, blood cells, cell fragments, platelets, salts and other soluble or dispersed blood constituents. All of these are included in the term "debris". Cleaning permeable membranes is more difficult than cleaning solid surfaces, because whatever is held back by the membrane can lodge either immediately at the membrane exposed surface or within the membrane pore structure, with the surfaces within the membrane pore structure being more difficult to clean.

At present hemodialyzers are typically re-used up to about 30 times. However, for some patients, who may represent roughly one-quarter of hemodialysis patients, hemodialyzers clog more quickly and thus can only be re-used three or four times. A better method of cleaning and disinfecting hemodialyzers between uses could extend their useful life, with consequent economic savings, and possibly improve the biological performance of reused hemodialyzers. Even if the improved cleaning only extended the life of those hemodialyzers which are presently re-used three or four times up to re-use of up to 15 times, the economic savings would be considerable.

Membrane filters, at present, are cleaned with harsh liquid-phase chemicals and/or large quantities of hot water, including backflushing. Even though such membranes are cleaned at regular intervals, they never return to their original flux levels. Essentially, this constitutes a permanent de-rating of the membrane's capacity.

In all of these applications and geometries, better cleaning methods for passageways would be useful to more completely and easily remove the biofilm, debris, contaminants and the like. In any filtration application an improved cleaning method would either extend its membrane life or improve the performance of the processing.

For medical/dental applications a thorough cleaning is a very important first step in disinfecting or sterilizing the equipment. A good initial cleaning makes any subsequent disinfection or sterilization procedure easier and more effective by reducing the bioburden which has to be killed during disinfection or sterilization. At present the major forms of sterilization are heat, harsh chemicals and radiation. Some medical devices contain materials or components which suffer damage from one or more of these processes, or there may be times when for other reasons it may be impractical to use them. Thus improved methods of disinfection or sterilization which stay close to ambient conditions, use benign chemistry, and are simple to perform would be broadly useful for many medical and industrial applications. Thus, improved methods of cleaning regular and irregular surfaces and passageways of various medical devices, as well as devices in contact with food or potable water, or those that need to be made sterile, methods that can be carried out rapidly, effectively and inexpensively, and that do not employ extreme temperatures, harsh or toxic chemicals or radiation, would be highly desirable.

SUMMARY OF THE INVENTION

In accordance with the method of the present invention, a mixture of gas and a suitable liquid, preferably including one or more cleaning agents, is used to create a mixed-phase flow along a surface, which creates shear or impact stresses or similar conditions sufficient to remove biofilm, debris and contaminants from their surfaces. The cleaning agent is commonly a surfactant, but may also be or include an oxidizing agent, an alcohol, a non-surfactant detergent or a solid material. The method may be applied to passageway geometries of considerable complexity, including surfaces made of a porous membrane. It further includes optimally varying parameters such as the fluid mechanics regime of the mixed-phase flow, the chemistry of the cleaning liquid, temperature, and, in the case of membranes, the direction, magnitude and sequencing of pressure differences across the membrane.

BRIEF DESCRIPTION OF THE DRAWING

FIGS. 3A and 3B illustrate the geometry of a biopsy device that can be cleaned by the method of the invention.

DETAILED DESCRIPTION OF THE INVENTION

Figure 1:
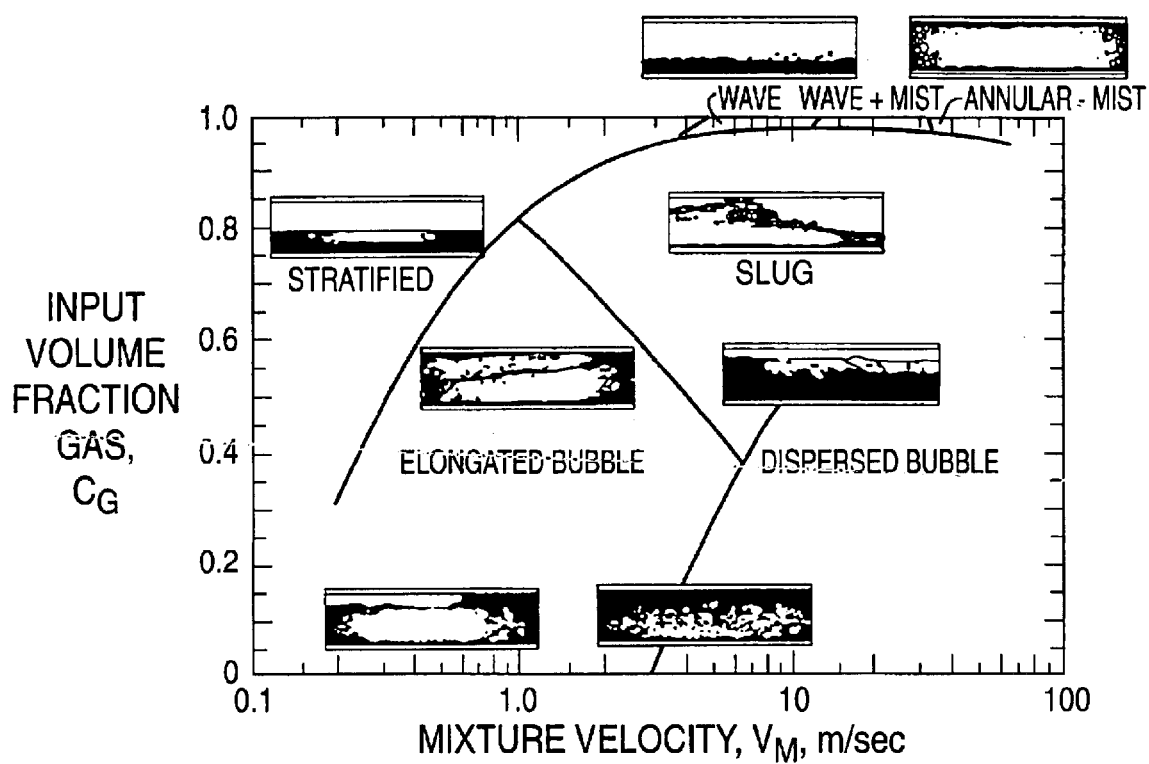
FIG. 1 shows a map of regimes of two-phase fluid flow in a horizontal orientation.

The present invention is directed to a method of cleaning various irregular surfaces and passageways. Typically the surface or passageway is long and narrow; it can be of a complex shape; and it can be described by the ratio of its length to width or diameter. The passageway may or may not carry fluid during normal use, but it is capable of carrying mixed-phase fluid flow during the cleaning procedure. A mixed-phase flow is passed along the surface to dislodge and remove various materials such as biofilm and other forms of biological and non-biological debris and contaminants.

The term "biofilm" as used herein denotes bacterial colonies that grow on a surface, and their associated organic matrix materials.

In order to describe the present invention, it is helpful first to discuss some background information about fluid mechanics, geometry and chemistry. It is known that in order to remove biofilm from a solid surface, a local shear stress, generally of 53 Pa or more, is required. The difficulty of removing biofilm from a surface can vary with the age of the biofilm and the nature of the surface, generally becoming more difficult as the biofilm gets older. It can also depend on the specific bacteria which produced the biofilm. When conventional cleaning using a steady flow of liquid solutions is carried out in a long narrow passageway, which results in an overall pressure drop along the passageway, it is likely that the velocity would be quite small and the resulting wall shear stress would be too low to remove biofilm, debris or contaminants. If the same passageway were cleaned with a steady flow of a gas alone, the gas velocity could be much higher for the same overall pressure drop, but sufficient wall shear stress still could not be obtained because the viscosity of the gas is low.

In fact, for constant-cross section steady flow of any incompressible single-phase fluid, the achievable shear stress can be calculated from a control volume view with no reference at all to specific fluid properties. In any given application there is some limit on the overall pressure drop from one end of the passageway to the other. This may be determined by the structural limits of the passageway wall or other device, or the desired overall pressure drop may be equal to the pressure available from pressure sources such as a typical compressor. The pressure range for which compressors are most readily available is approximately 100 psig. The force on the control volume is given by the overall pressure drop times the passageway cross-sectional area, and it is also given by the wall shear stress times the wall surface area. For a given allowable or desired pressure drop across a passageway, the wall shear stress is simply the pressure drop times the cross-sectional flow area divided by the total wall surface area. For circular tubes this further simplifies to $$\tau = \Delta p / (4 \ast L/D)$$

where tau is the shear stress at the wall, deltap is the pressure drop from inlet to outlet of the passageway, and (L/D) is its length to diameter ratio. Thus, the ability to produce a desired shear stress is not dependent on the fluid properties, or even on whether the fluid is a liquid or a gas. For long narrow tubing (large L/D) this shear stress is too small to achieve removal of biofilm. For typical conditions, using the above formula, the pressure drop might be 14.7 psi (100,000 Pa), and the L/D might be 1000 or more. This gives an average shear stress of 25 Pa, which is not enough to remove biofilm by itself, although it can be a contributing factor.

Cleaning, disinfecting and sterilizing can also be defined here. Cleaning refers to physically removing biofilm, debris and contaminants typically including bacteria and/or spores. Disinfecting refers to bacterial count, and specifically the reduction in bacterial count by a substantial fraction (at least six) orders of magnitude), although it is not necessarily perfect removal of every bacterium or spore. Sterilization refers to inactivating all microorganisms including bacterial spores.

The flow rate of a gas can be reported in standard volume units per unit time, which is really a mass flow rate and is constant everywhere along a steady-state flow to which nothing is added or taken away. Standard volume units such as standard cubic feet are defined at one atmosphere (absolute) of pressure and 0° C. The flow rate of gas can also be reported in actual volumetric units per unit time, which essentially is a geometric quantity based on the local velocity and cross-sectional area. This quantity depends on the absolute pressure of the gas at the site where the measurement is made, because the density or specific volume of gas depends on the absolute pressure. Therefore, in experiments such as the present ones, the gas flow rate in actual volume units will be different at different places along the flow path.

The mixed-phase flow has a high volume ratio of gas to liquid and certain combinations of liquid properties. The advantage of a mixed-phase cleaning system is that it combines the best of both liquid and gas flow. It can have an overall pressure drop per unit length which is acceptably small as governed mostly by the characteristics of the gas flow, but the liquid phase is moving with the gas at a substantial velocity. Therefore, at the places where the liquid phase interacts with the wall there can be high-velocity impact of the liquid in certain places and an accompanying high local shear or impact stress.

A droplet impact can produce a local instantaneous shear stress which is much larger than the average shear stress given by the calculation for single-phase flow. It can do this because its velocity can be close to or equal to the velocity of the gas, while the shear or impact stress it produces is related to the liquid viscosity and/or density, both of which are much higher than those of the gas. Thus the mixed-phase flow combines the best feature of the liquid, its high viscosity and density, with the best feature of the gas, namely the ability to achieve high velocity without excessive pressure drop per unit length.

The area of the wall cleaned by the impact of any one droplet or liquid film is limited, and at any instant of time, the area of the wall being cleaned is only a fraction of the total wall surface. However, when the process is continued for an appropriate period of time, given the generally random nature of the process, eventually every bit of the entire surface will experience a significantly large shear stress at some point in time and will be cleaned. Instead of experiencing a continuous shear stress, which is too small to do anything to the biofilm, debris and contaminants, each individual piece of the surface experiences for some, albeit brief, period of time, a much larger shear stress which does remove biofilm, debris and contaminants. However, since at any instant of time these interactions affect only a small portion of the wall surface, they do not cause a large overall pressure drop.

A further enhancement of cleaning action can be obtained by including solid particles in the liquid. Appropriate chemistry of the cleaning solution can also be helpful. The liquid cleaning solution is most commonly an aqueous solution, but it could also be another liquid. The gas is generally air, but any other gas can be used.

In a dispersed drop flow regime, when droplets impact the walls of the passageway, they spread out and form a sheet or liquid layer on the wall. In the fluid flow regimes which are desirable for cleaning, the sheet of liquid (on the wall or surface of the passageway exposed to the mixed-phase flow) may attain a thickness such that the moving gas can pull droplets away from the liquid layer. This is called entrainment. Entrainment depends on certain fluid properties and on the creation of hydrodynamic instabilities in the liquid layer. The instabilities are such that when a disturbed shape is created on the surface of the liquid layer, the liquid surface does not return to flat, but rather further deforms until drops are formed and ripped off. It is believed that when drops are ripped off, there may also be a force exerted on particles of biofilm, debris and contaminants at the place of departure of the newly-formed droplet. This force acts to detach and remove the biofilm, debris and contaminants from the surface to which they are adhering. It may be that the surface tension of the liquid helps to generate this force as a droplet is being removed from the surface.

For example, if a particle is wetted relatively fully on one side, while on the opposite side it is relatively dry, a force can be expected pulling away from the dry side toward the wet side. For certain combinations of wetting underneath a particle, and partial dryness on top of a particle, a force can be expected tending to lift the particle away from the surface. Since these forces are proportional to surface tension, this may be a reason not to pursue minimizing surface tension to extremely small values, and, in fact, the surface tension for water containing various salts can be slightly larger than that of pure water. However, surface tension which is somewhat reduced compared to pure water does promote the formation and ripping off of droplets from the liquid layer, which is good. When surfactants are used, they frequently have beneficial detergent effects.

There are also regimes found to exhibit good cleaning in which the flow is film flow, such as suds. As the flow moves, there is a continuous motion of and folding, stretching and regeneration of films. It is believed that when a film slaps into the wall as it moves, there may be an impact force analogous to that of droplet impact, and when a film pulls away from the wall or moves away from a particle of biofilm, debris or contaminant, there may be a removal force analogous to that just described.

Two-phase liquid-gas flow in tubes has been studied in such fields as boilers, electrical generating stations, chemical process plants, and pipelines. Knowledge tends to be somewhat empirical. There are various named regimes of liquid-gas flow such as bubbly, slug, plug, stratified, annular, entrained, froth and mist, with slightly vague demarcations between regimes. However, two variables have emerged as being most influential in determining the flow regime, and they have been used to create parameter maps which can be used to approximately predict regions for each flow regime. Such maps tend to be specific to one flow orientation, such as horizontal, vertical upflow, vertical downflow and the like. These two major variables are the volumetric ratio of gas to liquid, and the overall velocity.

FIG. 1 is such a map for horizontal flow, which is a typical orientation for medical and other applications where the present invention would be used. At low velocities and at small gas fractions, there tends to be distinct regions of gas, i.e., bubbly or stratified or slug, which may be described as gas dispersed in liquid. At higher gas-to-liquid ratios, the flow is no longer bubbles of gas surrounded by liquid, but rather becomes drops of liquid surrounded by gas (liquid dispersed in gas). Also, as the velocity becomes relatively large, droplets are broken away from liquid surfaces on the wall and are carried away (entrained). The regimes of interest for purposes of cleaning and disinfecting are regimes which occur at relatively low volume fractions of liquid (i.e., mostly gas on a volume basis) and at high velocity.

In addition to mechanisms such as the forces generated by surface tension, bubbles can be formed in the liquid, preferably near or at particles needing to be removed. One way to form bubbles is for gas to be dissolved in the liquid to come out of solution. Another way is to a gas by a chemical reaction.

In the case of a dissolved gas, a useful gas is carbon dioxide because it is relatively soluble in water. However, air can be used as well. The solubility of any gas in water is dependent on the absolute pressure to which the solution is exposed; thus a decrease in pressure can cause a gas to come out of solution and form bubbles. As liquid flows through a permeable membrane, depressurization occurs. On the upstream side of the membrane, at the higher pressure, a certain concentration of gas can stay in solution in the liquid. On the downstream side of the membrane, which is at a lower pressure, a smaller amount of gas can stay in solution, and the rest comes out of solution as bubbles. The bubbles form directly within the pore structure, where debris needs to be removed, and thus the debris is dislodged. The debris may serve as nucleation sites for the formation of bubbles. This is an efficient use of dissolved gas in a liquid. Two other gases which are significantly soluble in water are sulfur hexafluoride and nitrous oxide, although all gases are soluble in water to some degree. If oxygen or ozone is present in the gaseous phase, an oxidative or disinfectant effect can occur.

It is also possible to create bubbles from aa liquid by means of a chemical reaction which forms carbon dioxide or some other gas. For example, sodium bicarbonate can react with any acid, such as acetic acid, to form carbon dioxide. In such case the solutions which react to form a gas should not be mixed until they reach the place where bubble formation is desired.

Another way to create bubbles is by formation of vapor from the liquid. When the liquid is introduced into the passageway to be cleaned, it can be single phase, near its saturation condition. Then as the liquid flows through the passageway, the thermodynamic conditions would be changed to favor the existence of two phases, decreasing the pressure. This pressure decrease, due to the mixed phase flow progressing along the passageway, can also serve to liberate increasing quantities of dissolved gas as the flow continues, thereby providing bubble formation along the entire length of the passageway. Non-continuous pressure variations, such as surges, can be employed.

Although bubble formation has been described above for porous membranes, they are also applicable for cleaning nonporous applications, e.g., passageways with solid walls. The pressure drop that promotes bubble formation is the pressure drop which normally occurs due to flow along the principal direction of the passageway.

For the present cleaning method to be successful, one needs to understand the mechanisms of formation and re-formation of droplets. In the regime of entrained droplet flow (mist), droplets continually form and re-form as the mixed phase flow progresses down a passageway. After droplets strike or are deposited on a surface, liquid is eventually pulled out of the liquid layer to form new droplets, and the same action is repeated. In the lowest range of gas velocity, when gas flows past a liquid layer on a flat surface, the surface of the liquid will essentially remain flat and the liquid will be pulled along by shear. This is shown in FIG. 1 as stratified flow.

At somewhat larger gas velocities, waves will appear on the surface of the liquid layer as a result of the gas motion. This is shown as the wave regime. At still larger gas velocities, the amplitude of the waves becomes large enough that the shape of the surface becomes unstable, which is a hydrodynamic instability similar to the Rayleigh instability. This results in the breaking off of droplets which are then carried away by the flowing gas. This produces mist and is referred to as entrainment, and is also shown in FIG. 1 as the wave plus mist regime. As shown in FIG. 1, it exists at a mixture velocity of about 10 m/s up to about 40 m/s. The boundaries depend on local conditions and on fluid properties such as surface tension, viscosity and the like, but such maps have only been generated for a limited range of dimensions for common fluids such as watyer and occasional hydrocarbons, encompassing only a narrow range of fluid properties.

The annular-mist regime generally exists at a mixture velocity of over 40 m/s, up to about 100 m/s. Presumably in the wave plus mist regime, there is sufficient agitation to form mist, but there still is some liquid collecting on the bottom of the horizontal tube. In the annular mist regime, which is at the highest velocity, there is so much agitation that there is not much differentiation between the bottom of the horizontal tube and other portions of the tube wall. These mist regimes are favorable regions of operation for the present invention. In these regimes, the gas velocity is large enough to remove droplets from a liquid layer, and also the velocity of liquid droplets when moving with the gas is large enough that, upon impact, these droplets are capable of dislodging or eroding biofilm, debris and contaminants.

The present cleaning method is applicable to extremely long 1/D tubing, and it is especially useful to be able to re-form droplets on a continuing basis after the initial impact of droplets with the tubing wall. The ability to clean long lengths of tubing is a significant advantage of the present invention. This requires operating in the appropriate region of parameter space so that the gas is able to form and entrain droplets repeatedly by means of the hydrodynamic instability. It can be estimated that prior art techniques which use a total of only a drop or two of liquid would not provide enough liquid for the surface area of a dental handpiece tube to achieve significant re-formation of droplets. One or two drops equals tenths of a milliliter. The present method uses a continuous flow for a period of time such that the amount of liquid used for the same purpose would be tens of milliliters, some two orders of magnitude higher.

Additionally, some geometries which are capable of being cleaned by the present invention have abrupt changes of geometry such as right-angle elbow or U-bends. It might be expected that at such changes of direction, many of the droplets will impact the elbow or bend and coalesce, which presents a danger of depleting the population of droplets which are the supposed mechanism of erosion. Nevertheless, it will be shown hereinbelow that good cleaning using the method of the present invention has been observed in passageways which have as many as seven reversals of direction. This indicates that the appropriate mixed-phase flow condition re-establishes itself quite well within a short distance after such a disturbance.

The formation and re-formation of droplets is influenced by, among other parameters, the surface tension of the liquid, the viscosity of the liquid, and the velocity of the gas relative to a liquid layer on the wall. In regard to surface tension, it is believed that, particularly for small diameter tubing, it is important that the liquid have a lower surface tension than pure water, which is about 72 dynes/cm. The addition of typical surfactants can lower that value to as low as 17 dynes/cm, depending on the specific surfactant added and its concentration. It is believed that a surface tension lower than about 72 dyne/cm, but higher than about 17 dyne/cm, encourages the formation of an appropriately small droplet size. It is believed that such a size results in high localized shear stresses when a droplet moving at or near the gas velocity in the principal direction of motion makes contact with the stationary wall and exerts a viscous shear on the wall. Such a value of surface tension may also extend the region of shear by encouraging wetting of the wall, and it is believed to help in reforming droplets after initial impact with the wall. However, if the surface tension is rather large and the diameter of the passageway is small, slugs may form, see FIG. 1, a regime which does not achieve good cleaning. It has been discussed elsewhere that surface tension higher than that of pure water (even as high as 150 dynes/cm) can be achieved with certain additives and this may be desirable for one mechanism of removal of particles. It is believed that the surface tension which is best used for comparing to the values just discussed is the dynamic surface tension of the liquid at the time scale characteristic of the droplet formation processes, rather than the static surface tension. For some substances, static and dynamic surface tension are indistinguishable, but for other substances they are different.

A cleaning solution can be used without the addition of a surfactant, providing its surface tension is within the above parameters.

It is also believed that an extremely small surface tension is not desirable because the droplets might become too small. In such case the droplets follow the motion of the gas so completely that the droplets do not often impact the surface of the passageway to be cleaned, referred to as channelizing the flow. Thus that amount of surfactant is added that provides good cleaning both by virtue of re-forming of droplets and a requirement that the droplets follow the gas motion closely, but not too closely.

The viscosity of the liquid is also important. The viscosity of water is affected by additives, most additives acting to increase the viscosity. Too large a liquid viscosity may prevent the liquid from breaking up into sufficiently small droploets, and will result in the liquid staying attached to the wall after the first impact, which is deleterious to cleaning. We have found that 500 centipose (cp) is too viscous.

The volumetric ratio of gas and liquid is also important for achieving cleaning. As will be described hereinafter, typical ratios of gas (usually air) to liquid cleaning solution are 50:1 to 6000:1, with that ratio being considered to be the flow rate of gas at standard conditions, i.e., one atmosphere (absolute) of pressure and 0° C., relative to the volumetric flow rate of the liquid solution. If too much liquid is present, the regime of slug flow occurs, and it is difficult to achieve sufficiently high velocities and to achieve droplet formation and ripping off of droplets from the liquid layer on the wall. Too little liquid cannot achieve good cleaning in a reasonable period of time, simply because there are not sufficient droplets to impact the wall often enough. This could in principle be overcome by lengthening the treatment time, but at the expense of convenience. For a given source pressure, the flow rate of gas can be measured when only gas is flowing through the surface being cleaned. At the same source pressure, the flow rate of gas for mixed-phase flow is measured by placing the flow meter upstream of the mixing point. It is usually found that for conditions conducive to good cleaning, the gas flow rate for the mixture is at least 40% of the flow rate of dry gas alone.

Because the liquid droplets have a larger velocity near the exit than near the entrance of a passageway, the cleaning effectiveness is usually better near the exit and somewhat less efficient near the inlet, as influenced particularly by the velocities of droplets and the effect of droplet re-formation and the shear due to the gas flow itself.

It is believed to be advantageous if the main flow of the gas is turbulent. Turbulence in the gas enhances the ongoing reformation of the liquid droplets and also enhances the impact of droplets against the wall by providing, by means of the random turbulent fluctuations of local velocity, a velocity component perpendicular to the wall which directs the droplets into the wall. In general, turbulence in a single-phase fluid occurs at a Reynolds number above about 2000 or 3000. Since in the present invention the volume fraction of liquid will be rather small, the existence of turbulence can be estimated by the Reynolds number for the gas flow. There are some applications where it is unlikely that a gas Reynolds number in the turbulent range can be achieved, primarily because the diameter or characteristic dimension of the passageway being cleaned is small. This is the case, for example. in hemodialyzers and perhaps in other hollow fiber filters. In these instances, it has been observed that satisfactory cleaning still occurs even at a Reynolds number of several hundred. This implies that, although turbulence is helpful, the most important requirements are probably a sufficient velocity of the gas combined with the appropriate gas/liquid ratio and the appropriate chemistry.

In this case, a gas velocity or Reynolds number as large as reasonably achievable is desirable, since the velocity would still be significantly larger than a velocity achievable with water, or similar liquid, alone. In low Reynolds number flows, droplets may interact with the passageway walls that are not straight, or because at small passageway diameters, droplets may be a substantial fraction of the passageway diameter and may reach the surface simply because of size. Also, even though the overall flow would be laminar, it still may be possible to achieve some useful local velocity fluctuations at entrances, through the use of unsteady flow situations, such as by pulsating flow and the like.

A pulsating flow is an alternately stronger flow and weaker flow in a given direction, or could even involve repeated stopping or reversing of the direction of flow. Such disturbances or irregularities or unsteadiness may cause fluctuations in the gas flow which can be useful in causing localized secondary flow, or unsteady flow, which causes droplets to interact with the surface to be cleaned. Droplets interacting with the surface should provide the shear stress needed to completely clean the surface, as long as they have reasonable velocity and sizes. It may also be that in such situations, removal of debris is achieved to a significant degree by the ripping off of droplets from the liquid layer as described above.

The pulsating gas flow can also be turned completely on and off; during the off periods, the liquid flow continues. Thus some extra liquid accumulates inside the passageways during the off periods, and when pressure is re-applied, there is a surge of flow as the fluid containing a higher liquid fraction is rapidly accelerated. This surge will clean debris that may already be partially dislodged.

Over the course of several minutes of treatment to remove biofilm, debris and contaminants, the removal rate is slow at the beginning. However, the attachment of the biofilm, debris and contaminants to the surface is being weakened. Eventually, some biofilm, debris, and contaminants come off, and this assists in the removal of neighboring or connecting biofilm. This is particularly true of blood clots, The drag of the fluid, particularly in a surge mode, will in turn transmit a force to a part still attached and pull it from the surface. In all cases, the removal of some part exposes new surfaces and edges of biofilm which can then be removed, or the mixed phase flow can penetrate under the edge, and begin removal of the biofilm, debris and contaminants.

At least for some applications, the optimum method may be an essentially steady flow of mixed phase flow for most of the cleaning period, followed by the above-described pulsating flow for a portion of the cleaning time.

In addition to the just-described mist regime, the regime of film flow or foam is useful for cleaning, even though such a flow contains perhaps no droplets at all, but rather a multiplicity of films such as are found in soap bubbles. Film flow is essentially a large number of interacting films (which might also be terms suds) being pushed through a passageway. When film flow progresses down a passageway, there is believed to be an ongoing process of films bursting or striking the wall or being absorbed onto the wall and new films being regenerated by the stretching or rearranging of existing films. This can act to remove biofilm, debris and contaminants, especially if the film flow is pushed through at a substantial velocity. Foam is essentially film flow which is relatively thick, or has a relatively large apparent viscosity, generally having a smaller fraction of gas and a larger fraction of liquid. If a foam has an apparent viscosity which is so large that it is difficult to push the foam through a passageway at any significant velocity, little cleaning is accomplished. However, if the foam is thin enough (low volume fraction of liquid compared to gas) that it can be forced through passageways at a velocity useful for cleaning, cleaning will be successful. Also, even a foam which is too thick to be useful for cleaning can be useful for soaking. Perhaps the reason why film flow or a little bit of foaminess is useful for cleaning is because the film or foam counteracts the tendency of some flows to channelize, by catching droplets. Thick foam can be thought of as resembling shaving cream, while film flow or light foam is more desirable for the present invention.

It can also be realized by observing a mixed-phase cleaning flow propagate through a clear plastic tube, that there need not be a sharp boundary between the droplet flow regime and the film flow, or foam regime. Rather, there can be a gradual progression, with the flow starting out as droplets and becoming more like film flow or foam as it progresses along the passageway. Distinguishing between the physical properties of regimes is not always clear-cut because there can be regions where the flow is not clearly in either the droplet flow regime or the film/foam regime. Flows can even be unsteady and alternate between the regimes. Foaminess is also influenced by antifoaming agents. In order to achieve good cleaning, conditions appropriate to mist flow is used; for example, high gas velocity is still important.

If the gas velocity cannot achieve 10 m/s identified on the two-phase flow map as the boundary for mist flow in horizontal two-phase flow, cleaning can be possible anyway. For example, using a hemodialyzer, cleaning was attempted in the vertical direction, and a useful amount of cleaning was accomplished. It is possible that some geometric orientations are more tolerant of low gas velocities than others. It can be estimated that successful cleaning applications can involve gas velocities as low as 1 m/s.

It is also believed that if there are local fluctuations of pressure, gas may enter between the biofilm and the solid surface during a time of high pressure and then, when the pressure is low, may expand and tend to lift up the biofilm, thereby breaking it off. To achieve this, it is possible to provide pulsating flow. In some regimes of two-phase flow, the fluid behavior is naturally unsteady and this would provide some pressure fluctuations. In addition to the breaking off of biofilm, debris and contaminants, the overall flow flushes the broken-off biofilm, debris and contaminants out of the passageway.

In addition to passing mixed-phase flow through the passageway, additionally soaking the passageway for a period of time to soften the materials to be removed may be helpful. In such case, the liquid or foam present in the passageway is either stationary or only moving slowly. It may also be useful to use a sequence of cleaning, soaking and cleaning again. In addition to cleaning of solid surfaces which has just been described, the present invention can also be used with membranes, which have porosity and for which biofilm, debris and contaminants can lodge within the pore structure as well as on the overall surface.

In conventional cleaning, many porous passageways can be cleaned by causing a pressure difference across the membrane so that the pressure on the non-contaminated side is greater than the pressure on the contaminated side (referred to as backflushing). In this way, debris can be forced out of the pores back to the surface from which it entered. This technique can be advantageously used with the present invention involving mixed-phase flow in that particles of biofilm, debris and contaminants may be forced out from their locations within the pores by the pressure difference of backflushing and be forced into the mixed-phase flow and then immediately be removed by the flowing mixed-phase flow.

There are other combinations of flow conditions which can result in cleaning according to the present invention, as long as there is mixed phase flow on the side of the membrane which contains the biofilm, debris and contaminants. For example, the lumen side of the membrane containing the biofilm debris and contaminants can be exposed to a mixed phase flow and the other side of the membrane can be exposed to a higher pressure of either liquid similar to what has already been described, or a gas, either of which would serve to push biofilm, debris and contaminants out from the direction from which the came into the pores. Under the same conditions of mixed phase flow inside the lumens, the dialysate side of the membrane may be left unpressurized and some cleaning will be achieved, although this method is not as desirable.

Another sequence which may be useful is cleaning with the flow in one direction, and then reversing the inlet and the outlet and performing the cleaning procedure with flow in the opposite direction. It has been previously described that cleaning may be somewhat more efficient near the outlet of a long tube than it is near the inlet, because of the larger gas velocity near the exit. In this way, each end of the tubing is the exit end for some period of time, and so experiences the best cleaning. However, this does increase the cleaning time.

Another example when cleaning in both directions might be particularly useful, is the shell side of a shell and tube geometry such as a heat exchanger, a hemodialysis cartridge or ultrafiltration cartridge, where the geometry forms a dead end and has a high irregularity because of the large numbers of fibers entering the end cap. It is believed that cleaning of a dead-end may be more effective with flow directed into the dead end and leaving through a branch, as contrasted with the opposite direction of flow. It is believed that the former flow would create more turbulence which enters the dead end region and creates a scrubbing action. Since there are two dead ends (one at each end of the device) it would probably be advantageous to flow first in one direction, and then to reverse flow and flow in the other direction. In regard to dead-ends, depending on the design of the device, it may be possible to design a connector which advantageously directs flow into the dead end.

It may be desirable to perform the mixed-phase cleaning procedure of the invention first for a period of time with one cleaning solution and then for a period of time with another cleaning solution. In particular, typically in medical practice, a first step performs a more mechanical step of cleaning so as to remove gross amounts of biofilm, debris and contaminants, and a second step performs a more germicidal step which may be chemical, thermal and the like. It is possible to perform both types of steps with mixed-phase flow. If it is desired that the process be identifiably distinct as to the steps, the more mechanical step of removing gross amounts of biofilm, debris and contaminants can be performed using mixed-phase flow with a liquid cleaning solution as described above, and the other step using mixed-phase flow carried out using a germicidal cleaning solution. This last cleaning solution can include oxidizing agents, biocides or an alcohol. Another example when sequencing of liquid cleaning solutions is desirable is when the debris to be removed is of more than one type, such as both organic debris and inorganic scale, such as calcium carbonate and the like. For organic debris, an alkaline cleaning solution is preferable, while for inorganic scale, an acidic cleaning solution is preferable. These solutions are applied sequentially.

Finally, it may be desirable to provide the liquid cleaning solution, or the gas, or both, at a temperature somewhat above ambient temperature, because in general cleaning is improved at elevated temperatures. For elevated temperatures, in the case of shell and tube type geometries, and more particularly for small-dimensioned devices such as hemodialyzers, it is probably easier to maintain a large flow rate through the shell region as compared to the tube region. Thus, the flow through the shell region could be warmed in addition to or instead of warming the mixed-phase flow, to assist in warming up the entire device and maintaining it at temperature. The entire device could also be warmed as well.

After the above cleaning sequences have been carried out, the cleaned surfaces may also be rinsed or flushed to remove any traces of the cleaning agents which were added to form the liquid cleaning solution. When the liquid cleaning solution is water-based, this may be performed with water or it may be carried out using a two-phase solution of water and gas, either at the mixing ratio previously used, or at some other mixing ratio which is optimal for rinsing. Rinsing refers to a mixed-phase flow containing pure liquid, and flushing refers to all-liquid flow. Lastly, the procedure may also comprise drying the passageway using dry gas. With conventional liquid chemical disinfection or sterilization procedures it is common that the next-to-last step is a rinse with alcohol or an alcohol solution such as 70% alcohol in water, followed by drying with a dry air flow. This could easily be carried out with the present method.

In the case of weak adhesion, mixed-phase flow containing only a gas and a pure liquid such as water or alcohol, may be sufficient to effect good cleaning. However, important additional benefits can be obtained by adding a cleaning agent to the liquid It is known that surfactants can penetrate the residue to be removed and diffuse at the interface between the residue and the surface to be cleaned. This causes weakening of the bonding and adhesion forces at this interface, increasing the distance between the residue and the surface, which is commonly called the steric effect, and in some cases, increasing their electrostatic repulsion. This action, when combined with the mechanical action of mixed-phase flow, promotes faster and more efficient cleaning and removal of residues. The surfactant composition of the liquid cleaning mixture is therefore important, as are the pH and the oxidation potential of the cleaning liquid. Soluble inorganic compounds that have surface cleaning abilities can also be added. Surfactants typically have a molecular structure which has a hydrophilic head and a hydrophobic tail. The surfactants used in the liquid phase can include a plurality of surfactants, including anionic, cationic, nonionic and amphoteric types.

Suitable anionic surfactants include fatty acid soaps covering a range of alkyl chain length up to about 18 carbon atoms and may be straight or branched chain alkyl groups. These surfactants are normally used at a pH higher than the dissociation constant of their corresponding carboxylic acid. Another class of anionic surfactants that has been found to be effective with the present method is alkyl sulfates and sulfonates, such as sodium dodecyl sulfate (SDS). Yet another useful anionic surfactant may be based on alkylpolyoxyethylene sulfate. Another anionic surfactant that can be used is an alkylbenzene sulfonate. Linear and branched chain alkylbenzene sulfates with one or more sulfonate groups have been found to be useful. Suitable anionic surfactants also include alpha-olefin sulfonates, monoalkyl phosphates, acyl isothionates, acyl glutamates, N-acyl sarcosinates and alkenyl succinates and the like that have an anionic surface group and possess surface activity.

Suitable amphoteric surfactants include alkyldimethylamine oxides, alkylcarboxy betaines, alkylsulfobetaines, amide-amino acid type amphoterics and others that may exhibit amphoteric and surface activity. Amphoteric substances have characteristics of both acid and alkali groups.

Useful nonionic surfactants include polyoxyethylene alkyl ethers, polyethylene alkylphenyl ethers, polyethylene fatty acid esters, sorbitan fatty acid esters, polyethylene sorbitan fatty acid esters, sugar esters of fatty acids, alkyl polyglycosides, fatty acid diethanolamides, fatty acid monoglycerides, alkylmonoglyceral ethers, fatty acid polypropyleneglycol esters and the like.

Cationic surfactants useful herein include alkyltrimethylammonium salts and their phosphonium analogues, dialkyldimethyl ammonium salts, alkylammonium salts, alkylbenzyldimethylammonium salts, alkylpyridinium salts and the like which bear cationic functional groups and possess some surface activity.

Polymeric dispersants are also useful herein. Although they do not have the molecular structure of a typical surfactant, they have similar effects. These include formaldehyde condensates of naphthalene sulfonate, sodium acrylates or copolymers of other acrylic acids, copolymers of olefins and sodium maleate, lignin sulfonates, polyphosphates, silicates and polysilicates, carboxymethyl cellulose, cationic cellulose, cationic starches, polyvinyl alcohol, polyethylene glycol, polyacrylamides and the like. These compositions are also useful herein as surfactants. There are also detergent substances which are not strictly surfactants. Examples include trisodium phosphate, sodium-carbonate and polymers. Such substances can also be used with the present invention.

Another factor is the degree of foaminess that is created by the use of the surfactant. As already described, some degree of foaminess is believed to be helpful for cleaning. However, excessive foaminess decreases the velocity of the mixed phase flow and sometimes leads to near stoppage of the flow. Therefore, either the surfactant(s) used in the liquid cleaning solution must possess intrinsically low foaming properties, or else an antifoaming or defoaming agent can be added to the cleaning solution. Such agents are known and are commercially available.

Another important parameter in the cleaning liquid is its viscosity, since the liquid viscosity affects the mechanical action of the mixed flow cleaning method. In the case of aqueous solutions, the viscosity of the cleaning liquid can be adjusted upward if desired by adding water soluble polymers, such as carboxymethyl cellulose, hydroxyethyl cellulose, polyacrylic acid or any other viscosity increasing agents.

Chelating agents such as citrates, phosphates and ethylenediamine sodium salts and the like are useful in some applications for reasons including water softening, and to promote the removal of inorganic scales from some surfaces such as the surfaces of water pipes, heat exchangers, membranes and the like.

It is also possible to add a humectant into the formulation. A humectant is absorbed into the debris and in turn absorbs water, which helps loosen the debris. Suitable humectants include glycerol, sorbitol, ethylene glycol and the like.

The optimum pH of the cleaning solution depends on the nature of the material to be removed. For removal of organic deposits, an alkaline solution is preferred. PH adjusting additives can be used, as is known in the art. For removal of inorganic deposits, such as scale, an acidic solution is preferred.

An example of a useful non-surfactant aqueous solution is alcohol in water. One particularly appropriate alcohol is ethanol, which is widely used as a disinfectant but is not inherently toxic. The physical properties of alcohols, particularly ethanol, for surface tension and viscosity adjusting agents, are similar to those of water. Thus, an aqueous solution of alcohol will resemble water.

A biocide, a germicide or a disinfectant can be added to the cleaning solution, such as gluteraldehyde, or peracetic acid. Peracetic acid exists only in equilibrium with some concentration of hydrogen peroxide.

An oxidizing agent may be added to the liquid cleaning solution to help kill any bacteria which may not be physically removed by the mixed phase flow treatment. Oxidizing agents can be selected from oxygen- or chlorine-based agents such as sodium hypochlorite or sources of the same, and hydrogen peroxide or sources thereof, as well as other oxidizing agents. It is possible to form hydrogen peroxide from hydrogen peroxide precursors, such as percarbonate or perborate, while the flow is flowing through the passageway.

A catalyst can also be included to help the oxidizing action, as is known.

Ultrasound can also be used, either simultaneously with mixed phase cleaning, or at some other time. The ultrasonic vibration may help to loosen and dislodge biofilm, debris and contaminants, particularly in conjunction with the cleaning action of the mixed phase flow. This method is particularly appropriate for cleaning hemodialyzers, when the cleaning liquid fills the dialysate side, because ultrasound travels well through the dialysate side liquid to reach the fibers themselfes. The entire hemodialyzer can be immersed in a liquid bath which transmits the ultrasound, or by contacting ultrasonic transducers to the outside of the hemodialyzer, or any other way known by one skilled in the art.

A cleaning solution of particular utility herein is an aqueous solution including hydrogen peroxide. Since hydrogen peroxide decomposes to form free oxygen, oxygen is available to oxidize organic matter and kill microorganisms. Thus hydrogen peroxide cleaning with a mixed-phase flow is found to have better results in reducing bacterial count than cleaning with mixed-phase flow of pure water. Hydrogen peroxide is not a surfactant, but when hydrogen peroxide acts on biofilm, it chemically attacks the biofilm in such a way that it loosens the attachment of the biofilm to the surface. The loosened biofilm can then be flushed out of the system being cleaned. Another advantage of hydrogen peroxide is that its only other decomposition product besides oxygen is water, precluding any disposal problems.

Solid particles can also be added to the mixed phase cleaning solution. The particles added may be soluble or insoluble in water. Examples of suitable solid particles include water soluble sodium bicarbonate, and water insoluble calcium carbonate. Solid particles may provide a scrubbing action in addition to the mixed phase flow. It may also be advantageous for the solid particles to be a solid oxidizing agent.

An important advantage of this invention is that the time required to remove biofilm, debris and contaminants is relatively short, approximately several minutes. This is in contrast to liquid chemical disinfection which soak the passageway for durations of sometimes many hours or days, when they still do not physically remove the structural matrix of the biofilm.

Reference is now made to FIGS. 2 through 8, which illustrate the present invention in greater detail.

The cleaning method of this invention can be applied to the geometry of a simple round tube, such as dental unit water lines and water or fluid lines for other medical devices such as endoscopes, kidney dialysis equipment, or to more complicated geometries, such as tubes or conduits whose cross-section is noncircular, e.g. elliptical, rectangular and the like, or a closed curve. The tube or conduit can include within it some other internal component or components defined by boundaries which are its own closed curve or curves. This can, for example be an annular geometry with an internal tube or object, as shown in FIG. 2.

Figure 2:
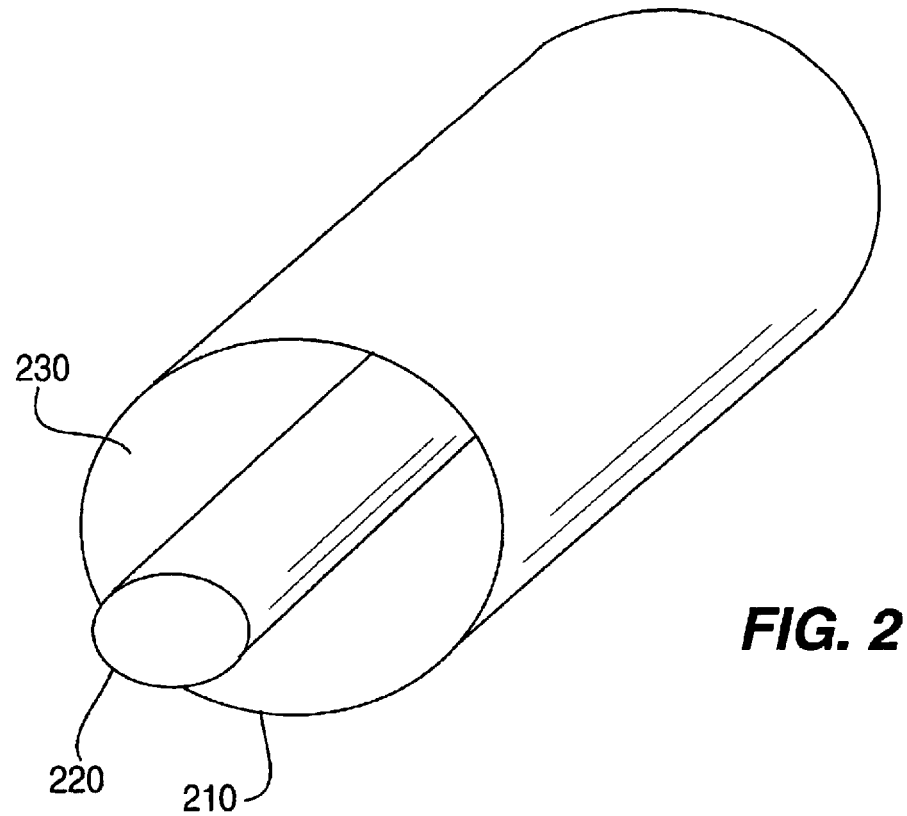
FIG. 2 illustrates an annular geometry that can be cleaned with the present methods.

FIG. 2 illustrates an outer tube 210, including therein an inner tube 220. The inner tube 220 is axial, but this is optional. In general, either outer tube 210 or inner object 220 or both could instead have a cross section of some other shape, such as elliptical or rectangular. The inner tube 220 may be a fluid-carrying tube or carry other components. The space 230 between the inner object 220 and the outer tube 210 has an annular cross-section and has a substantial length with two ends, defining a passageway. This passageway 230 carries mixed-phase flow during the cleaning process. This geometry is found in heat exchangers, catheters, biopsy devices, endoscopes and dental handpieces. The exterior of an endoscope may be cleaned by this method if the endoscope is enclosed in a temporary sheath, thereby defining an annular passageway 230 between the exterior of the endoscope and the interior of the sheath.

FIGS. 3A and 3B show a cross sectional view of a biopsy device 300. In FIG. 3A the biopsy device 300 comprises a central wire 320 which is surrounded by a sheath 310. The sheath 310 may be made of a helically coiled wire having multiple turns 315. The central wire 320 is moved axially relative to the sheath 310. At the other end is a device 350 for grasping, cutting and retaining a piece of bodily tissue when the central wire 320 and the sheath 310 are moved relative to each other. In order for mixed-phase flow to be introduced for cleaning, it is convenient to use access points already designed into the biopsy device, i.e., where wire 320 enters and leaves the sheath 310. This flow path is shown in FIG. 3A. If this is not practical and the coiled wire is bare, the coils may be temporarily stretched apart near one or both ends to provide flow space. In a typical commercially available biopsy device, the coil or sheath 310 is uncoated and the coils are capable of being stretched apart to provide access for the mixed-phase flow. In another commercially available biopsy device the coil or sheath 310 is coated, but at each end a suitable clearance exists so that flow can pass through the device to perform cleaning. Cleaning of the outside surface of the biopsy device can also be accomplished using mixed-phase flow by encompassing the exterior of the biopsy device into a tube of slightly larger diameter 380, as shown in FIG. 3B.

Figures 4, 5:
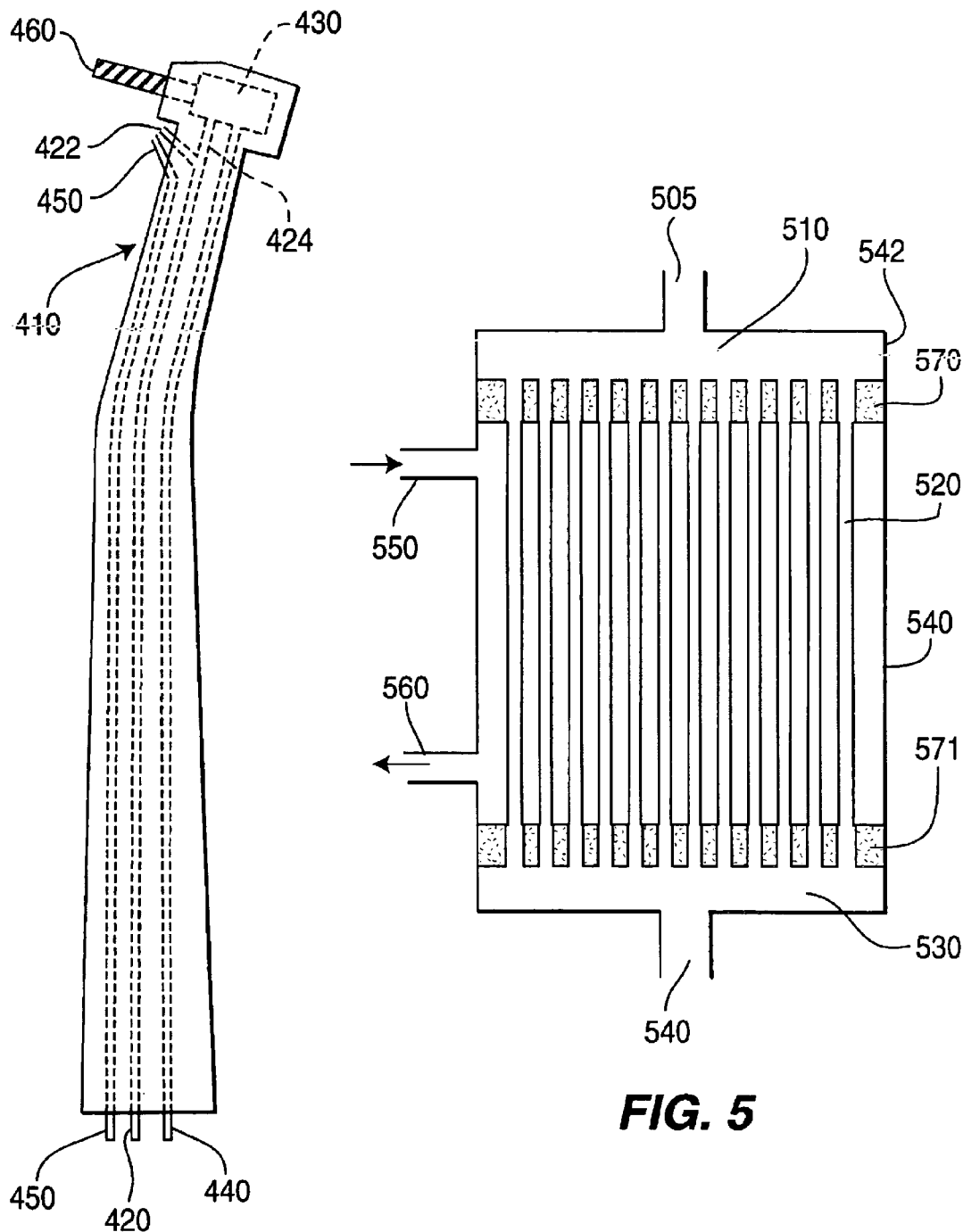
FIG. 4 illustrates a dental handpiece that can be cleaned by the method of the invention.
FIG. 5 illustrates a shell-and-tube geometry of various devices that can be cleaned according to the present method.

FIG. 4 illustrates a dental handpiece 410 for high-speed drills, which typically carries several fluid lines to and/from the drill 460. Inside the handpiece 410 is an air path comprising an air supply line 420 which bifurcates into a first branch 422 which is discharged as chip air toward the drill 460 to blow away chips. The air supply line 420 continues to a second branch 424 which leads to a turbine 430 and which then returns through return air path 440. Using the mixed-phase flow cleaning method, it is possible to simultaneously clean both branches 422 and 424 of the air path 420. Separately located within handpiece 410 is a water tubing 450 which discharges water to spray at the region of the drill 460. The water tubing can also be cleaned by the method of the invention.

Several variations on handpiece design are known and can be cleaned by the method of the invention. In some handpieces the chip air is discharged coaxially around the water discharge, so as to break up the water discharge into a spray; others have a completely separate fluid path and connection for the chip air instead of having chip air branch off from the turbine air supply. In another design, all of the fluid passageways are located coaxially where the handpiece joins the utilities supply cord. This creates some annular flow geometries as described earlier. In a more complex design, the return air from the turbine is made to flow into a space which is generally annular but which is subdivided at annular intervals. This can also be described as a number of passageways in parallel, with each passageway having an elongated cross-section. This irregular shape and cross-section also requires cleaning and can be cleaned using the present invention.

The method of the present invention is applicable to cleaning passageways containing other bifurcations or divisions as well. A cross section of a shell-and-tube-type heat exchanger is illustrated in FIG. 5. Fluid enters through inlet port 505 and is divided in an inlet heater 510 including a plurality of parallel, either circular or non-circular conduits or tubes 520. The other ends of the tubes 520 are connected to an outlet header 530 which leads to an outlet port 540. In FIG. 5 only 12 tubes are shown, but any number can be present. Flow which enters the inlet header 510 must divide into many individual paths and then must come back together into one path at outlet port 540. This description applies to both the flow of fluid during normal operation and the flow of mixed-phase fluid during cleaning.

Opposed to the tubes 520 is a shell 542. This shell 542 is housing or enclosure which surrounds the tubes 520 and contains the fluid to which the exteriors of the tubes 520 are exposed. The shell side has two fluid port connections, a first connection port 550 near one end of the shell, and a second connection port 560 near the opposite end of the shell. One of these is a fluid inlet and the other is a fluid outlet as shown by the arrows. Tube sheets 570 and 571 provide a structural connection between the tubes 520 and the shell 540 and a seal which separates the fluid on the tube side from the fluid on the shell side. The geometry seen by the fluid inside the shell 542 is somewhat irregular. Between ports 550 and 560, the flow is somewhat parallel to the interior objects which were described in FIG. 2. However, near the first and second fluid ports 550 and 560, there are places where the internal objects separate out from the flow and the flow transitions to the inlet port 550 and the outlet port 560 or vice versa. This also results in a type of dead-end passageway which is a special case as far as cleaning is concerned.

Some heat exchangers are constructed with U-shaped tubes inside a shell, or with still other geometries, and some heat exchangers involve fins of various geometries. The present invention is useful for cleaning any of them.

The preceding devices have solid surfaces. Devices which include porous surfaces are discussed below.

Devices for filtration, reverse osmosis and hemodialysis use membranes to separate particles, substances or macromolecules from a liquid, typically water, by allowing the liquid to flow through the membranes while preventing particles of other substances or macromolecules from flowing through the membrane, thereby separating them. The membrane has a large surface area and is frequently tubular, but not necessarily of circular cross section. A liquid such as water flows under pressure along a fluid passageway which is lined with or made entirely from a porous membrane material. Various membrane designs separate solids, bacteria, dissolved materials, viruses and the like from drinking water, wastewater, blood, food products and the like. Such filters can be used for the purification of brackish or salt water (desalination), and for the recovery of potable water from wastewater.

Figure 6:
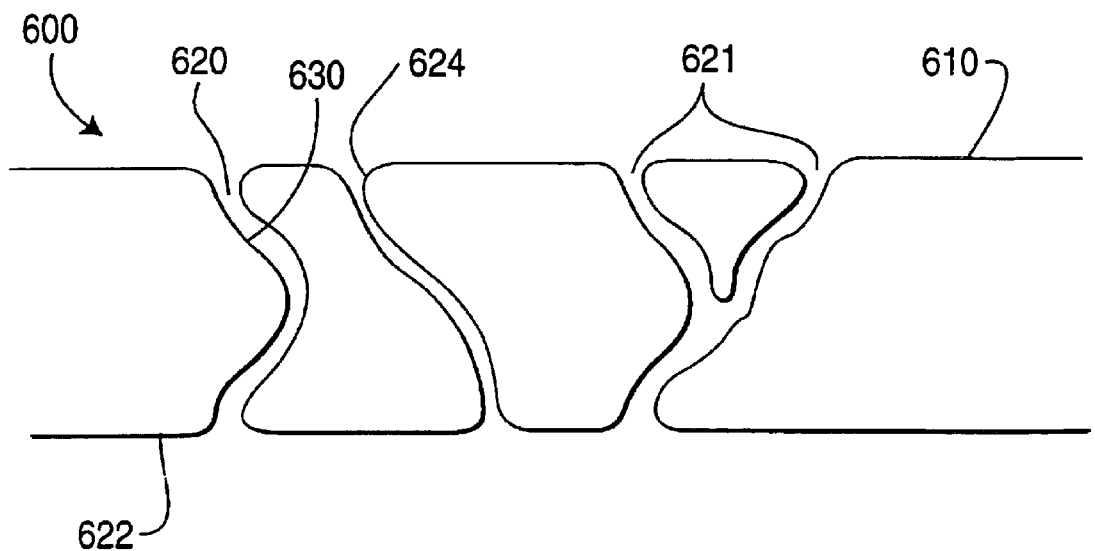
FIG. 6 illustrates the surface geometry of a permeable membrane that can be cleaned by the present method.

In addition to exposed surfaces, e.g., surfaces directly exposed to the mixed-phase flow during cleaning, the membrane has pore surfaces which are the surfaces of narrow passageways through the membrane. This is illustrated in FIG. 6, which shows a cross-section of a permeable membrane having the form of a tube. A membrane 600 has an exposed surface 610 on the side which faces the mixed-phase flow, and several pores 620 extending from the exposed surface 610 through the membrane 600 to its opposite surface 622. The pores 620 may be simple holes resembling tubes on a small scale, or, more likely, they form a three-dimensional network 621. In FIG. 6 curved corners 624 are shown where the pores meets the exposed surface. Cleaning such permeable membranes is more complex than cleaning solid surfaces because whatever is held back by the membrane can lodge either immediately at the membrane exposed surface 610 or within the membrane pores structure 620, which is more difficult to clean.

The method of the present invention can be used to clean both the exposed surface 610 and at least some of the pore 620. In order to remove solids from the membrane pores surface 610, it is necessary to thoroughly clean the membrane exposed surface 610, because if biofilm or other substances are not removed from the membrane exposed surface 610, they prevent particles and other contaminants from being removed from within the membrane pore 620.

As an example of such a membrane device, a hemodialyzer filter uses membranes to separate waste products from blood by allowing the waste products to pass through the membrane but not the desirable components of blood. A hemodialyzer works on the basis of osmotic differences, but some are microfilters, that is, a difference in chemical concentration between the two sides of the permeable membrane, and does not have as large a pressure difference across the membrane as does reverse osmosis and ultrafiltration. Typically the geometry in a hemodialyzer comprises a plurality of hollow fibers which can number up to about 15,000. The blood from the patient is on the inside of the hollow fibers and inside the headers at each end of the dialyzer. Thus the primary surfaces which must be cleaned and disinfected in order for a dialyzer to be re-used are the interior of the hollow fibers and the headers. The exterior of the hollow fibers are exposed to the dialysate, a fluid which absorbs and carries away waste substances from the patient's blood. A hemodialyzer may be used repeatedly. The pores of its membranes can clog with biological material, and the cross section of individual hollow fibers can also become blocked, leading to diminished performance.

The primary differences between a heat exchanger and a hemodialyzer are that the walls of the tubes are porous, and the tubes have different dimensions and proportions. As shown in FIG. 5, a hemodialyzer comprises a plurality of permeable narrow, hollow fibers (tubes) 520, all of which are connected to an inlet 510 at one end and to an outlet 530 at the other end. A housing 540 encompasses the tubes 510. The diasylate fluid enters the housing 540 at inlet 550 and exits through outlet 560. By applying the highest pressure to the ports 550 and 560, backflushing is carried out.

During the mixed-phase cleaning procedure, the fluid on the dialysate side can be, but does not have to be, circulated continuously. One useful function of the liquid on the dialysate side is that it can also be at an elevated temperature so as to help warm up the entire hemodialyzer and maintain it at temperature. Other means of heating the hemodialyzer are also possible, including convection, infrared radiation, preheating and the like. Of course, the mixed-phase flow inside hollow fibers 720 can itself be warm. It is believed that optimum cleaning will occur when the surfaces being cleaned are at a temperature which is higher than room temperature, but not so high as to cause irreversible chemical reactions in the deposited biological material, which might make it more difficult to remove.

In the case of a hemodialyzer, the permeability of the membrane is such that the quantity of water or liquid which seeps through the membrane during the cleaning process, if the dialysate side is pressurized to a higher pressure than the interior of the hollow fiber, may be sufficient to create the two-phase flow situation inside the hollow fiber. In this manner it may be possible to provide only flow of dry gas into the passageway. This gas flow would then become two-phase as a result of mixing with the permeated liquid. In this case the two-phase flow would have an increasing liquid content as it progresses from the inlet to the outlet of the passageway, due to additional liquid seeping in along the passageway. In itself, this variability of liquid fraction is not an intended feature of this mode of operation, but it may be convenient.

Geometries for filtration applications such as microfiltration, ultrafiltration and reverse osmosis, are similar to the shell and tube heat exchanger and the hemodialyzer. The one difference with respect to the geometries of a shell-and-tube heat exchanger or a hemodialyzer is that typically only three connections are actually used. On the side containing purified fluid, usually only one connection needs to be used because there is only outflow. The outflowing purified liquid is termed permeate.

Figure 7:
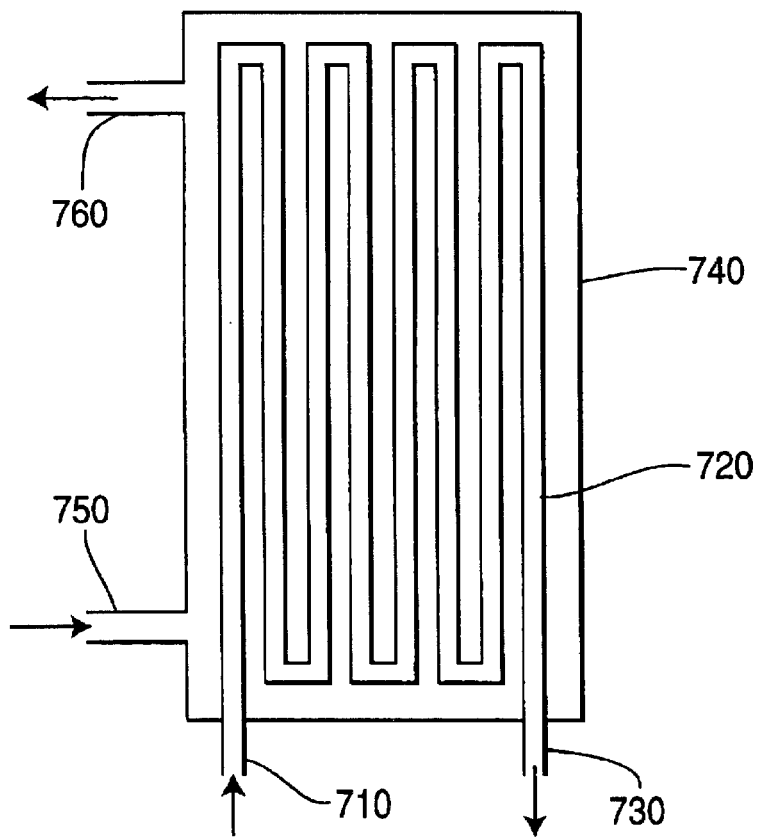
FIG. 7 illustrates another tubular filter design for ultra-filtration which can be cleaned by the method of the invention.

In the tubular filter of FIG. 7, the contaminated liquid flow path is one undivided flow path extending from the inlet 710 to the outlet 730. However, that flow path 720 may zig-zag back and forth a number of times, by means of return bends. Clean filtered liquid is collected inside the housing and can be withdrawn through either or both of the inlet and outlet ports 750, 760 through the boundary of the housing 740. The surface to be cleaned is the interior of the passageway from the inlet to the outlet.

Figure 8:
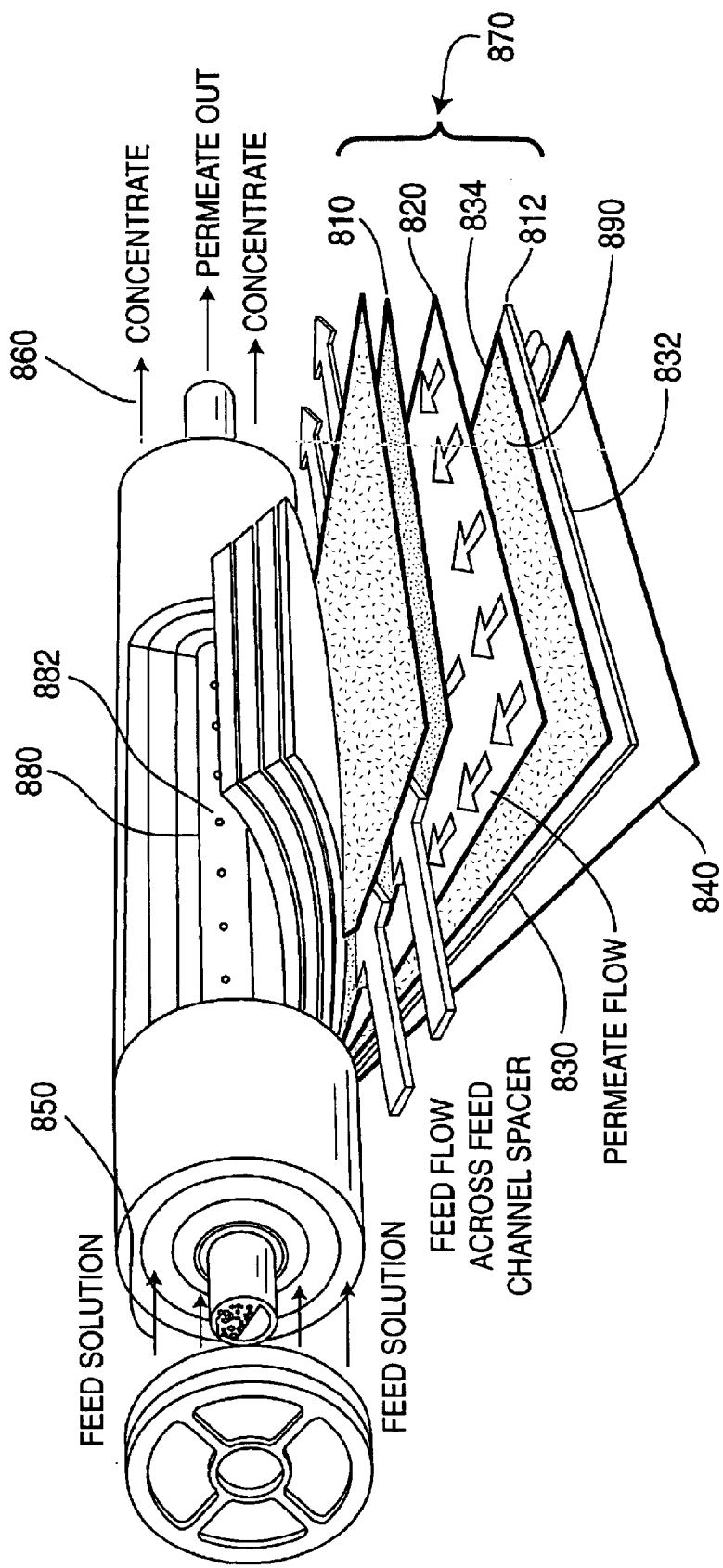
FIG. 8 illustrates a spiral-wound membrane filter cartridge which can be cleaned by the method of the invention.

There is another filter geometry which is used in filtration, ultrafiltration and reverse osmosis, called a spiral wound membrane filter as shown in FIG. 8. In this case, two rectangular membrane sheets 810, 812 are separated by a porous structural layer 820 and are sealed to each other along three edges 830, 832 and 834, forming a pocket or membrane assembly 870. A tube section 880 is manufactured with small holes 882 in a line along most of its length. Optionally, one end of the tube 880 may be closed. The membrane assembly 870 is attached in a leaktight manner to tube 880 such that the small holes 882 are exposed to the interior of the pocket formed by the two membrane sheets 810, 812. The membrane assembly 870 is then wound around the tube 880 in a spiral fashion, with a spacer 890 separating layers of the winding. Although FIG. 8 shows only one membrane assembly 870, it is possible for a filter to be constructed using more than one such membrane assembly, up to as many as twelve. Preferably, the junctions of the various membrane assemblies 870 to tube 880 are uniformly spaced about the circumference of the tube 880. The spacer 890 is typically a coarse mesh having the same overall dimensions as the membrane sheets 810, 812 and it may contain channels. The spacer 890 provides a flow path for contaminated liquid, allowing the contaminated liquid to contact almost the entire surface of the membrane sheets 810, 812. This entire rolled assembly is then placed inside a housing 840. Contaminated liquid is supplied to the outside surface of the membrane assembly 870, inside the housing 840. There are two ports 850 and 860 which connect to the housing 840 for the purpose of supplying and removing a flow of contaminated liquid.

Permeate flows through the membrane into the porous structural layer 820 which separates membrane sheets 810 and 812. The permeate moves through the structural layer 820 in a spiral path until it reaches the central tube 880 which collects the filtered liquid. In this example, contaminated liquid is supplied on the outside of the membrane assembly 870, between the membrane and the housing 840. Purified liquid is withdrawn through the central tube 880. Contaminants accumulate on all surfaces of the membranes 810 and 812 which are exposed to the contaminated liquid. The exposed membrane surfaces must be cleaned periodically to ensure proper operation of the filter assembly. It is difficult to clean these surfaces because they are inaccessible and restrict flow velocities. However, the method of the present invention is well suited for cleaning such filters.

Another geometry which can be cleaned by the method of the invention is one in which the flowpath divides into many parallel paths, as in a honeycomb, where there is flow of the same fluid on both sides of a passageway boundary. Such a geometry may be made of ceramic, and can be cleaned by the present method.

The present invention will be further described in the following examples. However, the invention is not to be limited to the details described therein. In the examples, water is distilled water.

EXAMPLE 1

This example illustrates cleaning of a dental handpiece having a complex internal geometry. The flow path of fluid through the handpiece is shown generally in FIG. 4, except that the return path is divided into a number of angularly spaced subdivisions. The internal diameter of the tubing varied from $1/32$ to $1/16$ inch. The tubing was thoroughly cleaned between experiments.

The handpiece was inoculated with an initial bacterial load of $4 \times 10^6$ Bacillus steariothermopholia spores (ATCC 7953) distributed among four chosen sites experimentally known to be the worst sites for cleaning.

The handpieces were then subjected to various cleaning techniques as set forth below. Then the cleaned handpieces were placed in sterile growth medium, and incubated for two days. The bacterial growth was then measured.

Part A. Surfactant Only.

The cleaning solution was a surfactant available as CPC-718 from VWR Scientific, which is a mixture of amphoteric and anionic surfactants. The solution was diluted to a 10% by volume solution with water. It had a pH of 10.5 at a temperature of 55° C. Air under pressure of 80 psig was passed into the handpiece for 15 seconds, a two-phase flow of air and solution passed through for five minutes, followed by a two-phase rinse with water for one minute. No bacterial growth was noted after two days.

Part B. Peroxide, No Surfactant.

The method of Part A was followed except that 3% of hydrogen peroxide and a mixture of transition metal organic complexes that improved the efficiency of radical generation in oxidation reactions was used as the cleaning solution. This solution had a pH of 10.4 and a temperature of 45° C. Air at a pressure of 80 psig was passed through the handpiece for 15 seconds, a two-phase mixture of air and the above solution for 3 minutes, followed by a two-phase water rinse. No bacterial growth was noted after two days.

Part C.

Dental handpieces manufactured by Star Dental, containing a complicated internal geometry, were used for this test. The cleaning reported here was for the flow path defined by the drive air plus chip air plus exit air circuit, similar in principle to the air flow path illustrated in FIG. 4. For the incoming part of the flow path, the geometry was a simple tube leading into the turbine and the chip air discharge, and for the exiting part of the flow path the geometry was the return path of air from the turbine. There is, however, a slight difference from the illustration in FIG. 4, in that the exiting flow path 440 was an annulus divided into a number of angularly spaced subdivisions.

EXAMPLE 2

The method of Example 1 was repeated but cleaning the internal water line channel of the dental handpiece, which was a simple tubular passageway. Similar results were obtained.

EXAMPLE 3

A biopsy device containing a cable inside a polymer-coated sheath, having an outside diameter of 0.084 inch, was used in this example. The access for fluid flow to clean the region between the cable and the sheath was at each end of the sheath where the cable entered or exited from the sheath using existing clearances. Cleaning between the sheath and the cable was tested by connecting the flow source to an existing threaded connection at the operator's end of the biopsy device. The flow then exited at the other end of the biopsy device where the tissue removal blades are located.

For cleaning the exterior of the biopsy device, the entire length of the device was inserted into a clear plastic tube which served as a passageway to direct flow along the outside of the device. The inside diameter of the clear plastic tube was about 50% larger than the outside diameter of the device.

Air was supplied at a pressure of 50 psi, and a gas/liquid flow rate ratio of several hundred to one, using sodium dodecyl sulfate surfactant in water. In both cases, the flow characteristics produced provided good cleaning, as determined by visual observation.

EXAMPLE 4

An ultrafiltration filter having about 300 hollow fibers, each having an inner diameter of 1.1 mm, was cleaned using the mixed phase cleaning method of the invention. The filter cartridge was about 7 inches long. The membrane material was polysulfone having a molecular weight maximum of about 100,000. The cartridge was designed to operate with permeate rates of 202 ml/min at 25 psi operating pressure. The interior of the hollow fibers were fouled with a mixture of Bovine Serum Albumin, calcium chloride and magnesium chloride.

Fouling was continued until the permeate rate was reduced to half of its initial flux. The fibers were cleaned using an aqueous solution of amphoteric surfactants at an air pressure of 15 psig for two minutes. The flux of the membrane was brought back to its initial value.

The above procedure was repeated except that the membrane was cleaned using a single phase flow of a solution of nonionic surfactant alone for 30 minutes. The permeate recovered to a rate of 134 ml/min or only 55% of its initial value.

The procedure was repeated except that the membrane was cleaned using a single phase flow of aqueous solution containing 0.25% of sodium dodecyl sulfate for 60 minutes. However, the permeate plateaued at a lower rate than its initial value.

The Reynolds number of the flow through the interior of the fibers can be calculated based on the known flow rate and cross-sectional area of air flow, the fiber diameter and the air viscosity. The calculated Reynolds number is in the upper hundred, which is within the laminar range. It is believed that cleaning action is best if the gas flow is turbulent, but this shows that even at the upper end of the laminar range, effective cleaning of hollow fiber ultrafiltration cartridges can be achieved.

EXAMPLE 5

Part A

A contaminated liquid was applied to the outside of hollow fibers of the same type of filter used in Example 4. The contaminating liquid was a mixture of gelatin and a dye. The cleaning solution contained sodium carbonate together with a surfactant "Tergitol", a trade name of Union Carbide Corporation. The air/liquid ratio was relatively wet at about 100:1 and the air pressure was 30 psig. The hollow fibers are rather flexible and, when wet, they can clump together which hinders cleaning. Thus the flow was pulsed and run for a somewhat longer period of time. Good cleaning was achieved.

Part B

The same geometry, i.e., cleaning of the outsides of a group of hollow fibers, can appear when there is no real housing at all about the fibers, but rather the fibers simply traverse open space between two headers that have some structural connection to each other. During normal use, the group of fibers is immersed in a body of possibly contaminated water, with clean liquid being withdrawn by suction from the insides of the fibers. Cleaning can be performed by directing mixed-phase flow at the exteriors of the hollow fibers. In such case it has also been found helpful to apply ultrasound simultaneously with the mixed-phase flow.

EXAMPLE 6

A rather large tubular filter, illustrated in FIG. 7, having a length of about 6 feet including 8 individual tubes connected in series so the overall flow length inside the tubes was 48 feet, having a flow path with a total of seven return bends of 180 degrees each, available from the Zenon Environmental Co. of Burlington, Ontario, Calif., was used as an ultrafilter during a wastewater treatment operation. The tubular membrane was Zenon MT-100 having a molecular weight maximum of about 100,000. The inside diameter of the tube was about 0.8 inch.

Waste water was supplied to the inside of this tube and clean water was extracted from the outside. During cleaning, the air supply pressure ranged from 40–80 psig. The flow rate of air was 120 standard cubic feet per minute. The velocity of the air was calculated to range from about 40 m/s near the inlet to about 175 m/s near the outlet. The Reynolds number of flow of air in these tubes was 225,000. The flow regime was film flow or light foam. The structure of this filter was such that it was not permissible to significantly backflush.

Part A

The filter was treated by a controlled synthetic wastewater until its flux decreased to 39% of its as-manufactured value. The filter was then cleaned by the two-phase cleaning method using several steps, including both acidic and alkaline cleaning liquids. The surfactant concentration of sodium dodecyl sulfate was 1%. Using an air:liquid ratio of 200:1, and an alkaline surfactant for 3 minutes, the flux recovered to 64% of its initial value. Applying the two-phase flow for another 2 minutes improved the flux to 81% of its initial value. Additional cleaning using hydrogen peroxide and a transition metal catalysyt did not improve the flux further. Only a slight improvement in the flux values were realized when the two-phase flow was reversed.

These results show that a total of five minutes cleaning of a tubular filter using two-phase flow is sufficient to restore the flux values and compares favorably with conventional cleaning requiring a much longer period of time. Repetition of the above cleaning gave similar results.

This experiment also illustrates the re-formation of the mixed-phase flow condition after a sharp change of direction. At each return bend it can be expected that there might be some disturbance of the mixed-phase flow condition, such as coalescence of droplets, but the successful cleaning results show that there is rapid re-formation of the mixed-phase flow condition after a flow irregularity, such as a bend.

Part B

In another experiment, the same type of filter was fouled by a controlled wastewater to the point where its flux level dropped to 35% of its initial value. Cleaning was performed and then stopped, while the flux was measured briefly using the controlled wastewater. Cleaning was resumed, and this was repeated several times until it became apparent that no further improvement was obtained. After three intervals of such cleaning, all at the same mixed-phase flow conditions, the flux level reached a plateau of about 74% of the baseline and no further improvement was obtained. To obtain further improvement, soaking was initiated because both the surface and pore structure of the tubular membrane had become fouled. For a period of time, the passageway was filled with foam which was stationary, and pressure continued to be applied in the same direction as normal operation of the filter. This allows the cleaning solution to reach deeper into the pores. This hold and soak cycle lasted 2 minutes, and was followed by the application of two-phase flow for 15 seconds to remove any newly-dislodged residue. The soaking brought a further improvement up to 95% of the baseline value.

Part C

Three additional filters were cleaned. Two of them had been fouled by normal use until the flux was about 40% of its initial value, and one had been fouled by normal use until the flux was only 4% of its initial value. All three were cleaned with a solution of an amphoteric surfactant and potassium hydroxide having a pH of 12.8. The cleaning cycle included several minutes each of two-phase flow and a holding period, with internal pressure under static conditions. A light backflushing was then performed using the liquid cleaning solution pressurized on the permeate side to several psi.

For the most heavily fouled filter, a further treatment was performed using an acidic two-phase flow cleaning for three minutes, followed by an alkaline two-phase flow cleaning for three minutes. The first two filters were restored essentially to 100% of their initial flux, and the last was restored to about 95% of its initial specified flux.

EXAMPLE 7

A typical hemodialyzer, Model 80B manufactured by the Fresenius Co. of Bad Homburg, Germany, was used. The internal diameter of a hollow fiber is 0.2 mm and the length to diameter ratio of each fiber is 1100. The 15,000 parallel hollow fibers were made of polysulfone. Experiments were performed on hemodialyzers which had been used for human patients, with reprocessing by conventional techniques after each use, until they failed the condition for re-use which is based on the total internal volume of the hemodialyzer (Total Cell Volume, or TCV). The hemodialyzers were then re-processed using the mixed-phase cleaning method. The mixing ratio was about 200:1 of air to liquid, and the cleaning solutions included surfactants and oxidants. The source pressure of the gas was 55 psig, and the flow rate was determined by how much flow of the mixed-phase mixture could pass through the 0.156 inch diameter inlet port and outlet port, the end caps of which were left on. The duration of treatments with mixed-phase flow was about 10 minutes.

The result was efficient removal of the proteins, blood cells and components from the lumens of the hollow fibers, as shown by SEM examination and actual TCV measurements. Improvement was visually observed in the condition of the end cap or header regions of the hemodialyzers after cleaning. After conventional cleaning, traces of blood were frequently visible in the header regions. After cleaning with two-phase flow, no such traces of blood remained.

The Reynolds number of the flow in the hollow fibers can be calculated based on the known flow rate and cross sectional area of air flow, the fiber diameter and the air viscosity. The calculated Reynolds number is about 200, within the laminar range. It is believed that cleaning action is best if the gas flow is turbulent, but even within the laminar range, effective cleaning of hemodialyzer cartridges. It may be that even though the attainable gas velocities are rather low for achieving significant droplet impact forces, the process of ripping off droplets from the liquid layer creates forces on the biological materials which have been deposited in the pore structure, or on the exposed surface, thereby assisting in their removal.

EXAMPLE 8

A hemodialyzer was cleaned by introducing an aqueous cleaning liquid including sodium bicarbonate into the dialysate side, At the same time, a solution including acetic acid was introduced in the form of mixed phase flow. When the two liquids came together near the membrane surface, the reacted to liberate carbon dioxide in the form of bubbles. Good cleaning was observed visually.

EXAMPLE 9

A hemodialyzer was cleaned by filling the dialysate side with a pressurized solut8ion of carbonated water. The pressure drop that the carbonated water experienced flowing across the membrane from the dialysate side to the lumen side caused bubbles of carbon dioxide to come out of solution. Good cleaning action was visually observed.

EXAMPLE 10

A hemodialyzer was cleaned with a cleaning solution including sodium hypochlorite, NaOCl. A two-phase cleaning solution including 0.25% of NaOCl resulted in good cleaning in ten minutes. The cleaning solution was pumped into the dialysate side and dry air was supplied to the interior of the hollow fibers, producing backflushing of liquid through the pores and two-phase gas-liquid flow inside the hollow fibers. In this case the cleaning solution as prepared for use contained no surfactant, and no sudsing could be generated when shaken.

However, when the cleaning liquid exited the hemodialyzer and was collected, substantial foaming was found in the collection vessel. Thus it is believed some chemical reaction occurred between the NaOCl and the organic materials deposited in the hemodialyzer pores that resulted in the creation of soap-like substances (saponification) which caused the foaminess in the collection vessel. Furthermore, it is believed that those soap-like substances may have further aided in the solubilization and removal of other protein substances from the pores of the membrane. It is also believed that the alkalinity of the NaOCl solution may also be of value in cleaning. The hemodialyser total cell volume was essentially restored to its initial value.

After thorough rinsing or flushing, the cleaning step is followed by a disinfection step using a disinfectant/sterilant, such as peracetic acid-hydrogen peroxide mixtures. The cleaning solution can be warmed up to about 130° F. which is less than the temperature which would denature protein.

Preferably, it is warmed only just before it is supplied to the hemodialyzer. Some pulsing of the liquid flow which occurred due to the operating characteristics of the pump, may also be advantageous. Pulsation and refersal of the gas flow are also advantageous.

Although the above example describes the possible interaction of NaOCl with organic matter to produce surfactant-like substances or effects, the addition of a known surfactant to the cleaning liquid may also be desirable. One suitable surfactant is Triton-X-100, which gives good performance. This nonionic detergent is often used in biochemical applications to solubilize proteins without denaturing them.

Another surfactant with similar properties is Cremophor EL, manufactured by BASF Corporation, an ethoxylated castor oil, and other members of that family. This product is already used for parenteral drug delivery in much larger quantities than a hemodialyzer patient could be exposed to. Chromophor EL is used for emulsifying and delivering the anti-cancer drug paclitaxel. A suitable concentration of either of these surfactants in the cleaning liquid is 200 ppm.

The cleaning solution containing NaOCl, either with or without a surfactant, is titrated with NaOH to a pH of 11.3.

During this cleaning procedure, clotted blood fibers several inches long could be seen exiting from the hollow fibers of the hemodialyzer, along with the mixed-phase flow. Polysulfone dialyzers in particular have limitations on the combination of concentration and time they can be exposed to NaOCl; however, a concentration of 0.225% NaOCl for about 10 minutes when warmed to 130° F. achieved good cleaning. Pulsation or on/off flow every few seconds and occasional reversal of the air flow direction through the hollow fibers were also employed. The TCV was restored to their initial values.

EXAMPLE 11

A spiral wound reverse osmosis filter manufactured by FilmTec Corp, a subsidiary of Dow Chemical Co., Model Number TW30-1812-50 was employed in this example. It is 10.5 inches in the axial direction and includes about 14 turns of wrapped membrane with a pore size which is appropriate to pass water molecules, but not large molecules. Purified water (permeate) is extracted through the central tube, while contaminated fluid accesses the filter through two ports, one at each end of the filter, one used as an inlet and the other as an outlet for concentrated contaminated water. Flux measurements were taken at differential pressures of 30, 50 and 70 psi. When the filter was new, the flux of pure water through the membrane was 38.6 mL/min at 30 psig, 86.4 mL/min at 50 psig and 133 mL/min at 70 psig. In all cases a flow rate of about 2300 to 2800 mL/min was maintained on the upstream side of the membrane, which was always at least 17 times as large as the flux of filtered water.

The membrane was intentionally treated with a synthetic mixture comprising Bovine Serum Albumin (BSA), NaCl and a suspended solid which included dried milk, soap, gelatin and starch. This mixture contains components which represent each of the three major mechanisms of fouling of reverse osmosis membranes, which are inorganic scaling, silting and biofouling. This mixture was pumped through the high pressure side for two hours at a pressure of 60 psig. This caused the membrane flux to be reduced to 13.2 mL/min at 30 psi, 48.8 mL/min at 50 psig, and 79.4 mL./min at 70 psig. Although the results differ somewhat from one pressure to another, most of these fluxes and their average are reduced to the range of 50–60% of the respective baseline flux values.

Several conventional cleaning sequences were performed involving only liquid phase (water and additives) being pumped through the contaminated liquid side of the filter.

The filter was cleaned with a solution of 0.5% of nonionic surfactant at 50 psi for 25 minutes. The flux recovered somewhat, to 26 mL/min at 30 psig, 55 mL/min at 50 psig and 96.3 mL/min at 70 psig, which is about 68% of their initial values.

Repeating the procedure using an anionic surfactant, 0.2% sodium dodecyl sulfate at 50 psi for 25 minutes, the fluxes were 19.2 mL/min at 30 psi, 53.4 m:/min at 50 psi and 89.8 mL/min at 70 psi, which showed no additional improvement.

Cleaning was continued with an acid cleaning solution of phosphoric and citric acids and a nonionic surfactant, but again there was no additional improvement.

Cleaning was then continued with a solution of NaOH and amphoteric and nonionic surfactants for 25 minutes, but the flux remained at about ⅔ of the initial values.

Cleaning was then performed for 3 minutes using a mixed-phase mixture of the invention. The liquid was a mild alkaline solution (pH 10.5) of water, EDTA and amphoteric, anionic and nonionic surfactants together with air under pressure of 65 psi, entering one and exiting another of the contaminated water ports. Some improvement was noted.

The mixed-phase cleaning was repeated with a higher flux of air, the air velocity being about 30–40 m/s. After 3 minutes, the filter flux returned to its original value. This is a significant improvement over conventional cleaning methods.

EXAMPLE 12

Clear plastic tubing having an inside diameter of about 2 mm in which biofilm had been grown was cleaned using a solution of hydrogen peroxide in water and a gas at a supply pressure of 60 psig. Complete removal of biofilm was obtained.

In contrast, a mixed phase mixture at a pressure of 60 psi was passed into the tubing for 3 minutes. The liquid was a solution containing 0.3% of Dowfax 9380 of Dow Chemical Co., a nonionic surfactant, 0.3% of F127 nonionic surfactant, 0.3% of Tween 20 nonionic surfactant and 1% of sodium carbonate in water. This mixture foamed so that little flow through the tubing occurred, and no cleaning was obtained.

Another solution of 0.2% of hydroxypropylcellulose in water was used. However, the viscosity of this solution is about 500 cp, 500 times greater than water, inhibiting the formation of droplets. Thus no cleaning was obtained.

Water alone was used to form a mixed-phase flow. In this case, because water has a high surface tension, it did not break up into small droplets which could follow the gas flow. Thus cleaning resulted in only a slight decrease in bacterial count. However, cleaning with water alone may be effective, such as when lightly adherent debris is to be removed from porous membrane surfaces.

A fluorosurfactant, Zonyl FSP made by DuPont Performance Chemicals in water was also tried. This solution had a surface tension of 25 to 40 dyne/cm, smaller than the usual detergent solutions. Cleaning was poor because at this low surface tension, droplets formed were too small to interact with the tubing walls.

Thus the mixed-phase cleaning method of the invention is applicable to solid passageway boundaries of any type, including plastics, metals, ceramics and the like. The method includes regimes of droplets dispersed in gas (froth, foam) and film flow which resembles a multiplicity of films such as soap bubbles. The exact boundaries of parameter space for good cleaning are difficult to define, because of the empirical nature of multi-phase fluid mechanics and because the requirements vary with the amount of cleaning desired and the time available. Generally, the gas flow rate when liquid is added is at least 40% of the gas flow rate when no liquid is added. In general a supply air pressure of 60–100 psi is useful, but for some purposes supply pressures as low as about 15 psig can be used, attainable with blowers rather than compressors.

It will be apparent that various cleaning solutions, temperatures, pulsation, soaking, sequential passage of solutions, with or without a pressure difference as across a membrane either to force cleaning solution into the pores or in reverse direction to force contaminants out of the pores, can be used. Solid particles, soluble or insoluble, can also be added to the liquid. A final rinse with water can be used, or an alcohol-water rinse to promote drying. The scope of the invention is not to be limited to the disclosure, but only by the scope of the appended claims.

We claim:

1. A method for cleaning a pipeline comprising:
   (a) forming a mixture of gas and liquid in the pipeline wherein at least a portion of the liquid is provided in the form of droplets; and
   (b) passing the mixture of gas and liquid through the pipeline at a flow rate and at a volumetric ratio of gas to liquid sufficient to provide a local shear stress at the inside of the pipeline of at least about 53 Pa and to provide the droplets throughout the length of the pipeline.

2. A method according to claim 1, wherein the volumetric ratio of the gas to the liquid is at least about 50:1 when measured at 1 atmosphere and 0° C.

3. A method according to claim 1, wherein the volumetric ratio of the gas to the liquid is less than about 6,000:1 when measured at 1 atmosphere and 0° C.

4. A method according to claim 1, wherein the mixture of gas and liquid is provided within the pipeline at a velocity of at least about 10 m/s.

5. A method according to claim 1, wherein the mixture of gas and liquid is provided within the pipeline at a velocity of at less than about 100 m/s.

6. A method according to claim 1, wherein the mixture comprises a cleaning agent comprising at least one of a surfactant, an oxidizing agent, an alcohol, and a non-surfactant detergent.

7. A method according to claim 6, wherein the cleaning agent comprises an anionic surfactant.

8. A method according to claim 7, wherein the anionic surfactant comprises at least one of fatty acid soaps having an alkyl chain length of up to about 18 carbon atoms, alkyl sulfates, alkyl sulfonates, and mixtures thereof.

9. A method according to claim 7, wherein the anionic surfactant comprises at least one of sodium dodecyl sulfate, alkyl polyoxyethylene sulfate, alkyl benzene sulfonate, alpha-olefin sulfonates, monoalkyl phosphates, acyl iosthionates, acyl glutamates, N-acyl sarcosinates, alkenyl succinates, and mixtures thereof.

10. A method according to claim 6, wherein the cleaning agent comprises an amphoteric surfactant comprising at least one of alkyl dimethyl amine oxides, alkyl carboxy betaines, alkyl sulfobetaines, amide-amino acid type amphoterics, and mixtures thereof.

11. A method according to claim 6, wherein the cleaning agent comprises a nonionic surfactant comprising at least one of polyoxyethylene alkyl ethers, polyethylene alkyl phenyl ethers, polyethylene fatty acid esters, sorbitan fatty acid esthers, polyethylene sorbitan fatty acid esters, sugar esters of fatty acids, alkyl polyglycosides, fatty acid diethanolamides, fatty acid monoglycerides, alkyl monoglycerol ethers, fatty acid polypropolene glycol esters, and mixtures thereof.

12. A method according to claim 6, wherein the cleaning agent comprises a cationic surfactant comprising at least one of ammonium salts, phosphonium salts, pyridinium salts, and mixtures thereof.

13. A method according to claim 6, wherein the mixture comprises a dispersant.

14. A method according to claim 6, wherein the mixture comprises an antifoaming agent.

15. A method according to claim 6, wherein the mixture comprises a chelating agent.

16. A method for cleaning a membrane, the method comprising:
   (a) applying a mixture of gas and liquid to a membrane in a housing, the mixture comprising the gas and the liquid phase at a volumetric ratio of at least about 50:1 when measured at 1 atmosphere and 0° C., and wherein at least a portion of the liquid is provided in the form of droplets and the liquid comprises at least one cleaning agent.

17. A method according to claim 16, further comprising:
   (a) rinsing the membrane with water.

18. A method according to claim 16, wherein the volumetric ratio of the gas phase to the liquid phase is less than about 6,000:1 when measured at 1 atmosphere and 0° C.

19. A method according to claim 16, wherein the membrane comprises at least one of ultrafiltration membrane and a reserve osmosis membrane.

20. A method according to claim 16, wherein the mixture is provided at a velocity of at least about 10 m/s.

21. A method according to claim 16, wherein the mixture is provided at a velocity of less than about 100 m/s.

22. A method according to claim 16, further comprising:
   (a) soaking the membrane with the liquid phase.

23. A method according to claim 16, wherein the mixture is provided at a temperature above ambient temperature.

24. A method according to claim 16, wherein the cleaning agent comprises at least one of a surfactant, an oxidizing agent, an alcohol and a non-surfactant detergent.

25. A method according to claim 16, wherein the cleaning agent comprises an anionic surfactant.

26. A method according to claim 25, wherein the anionic surfactant comprises at least one of fatty acid soaps having an alkyl chain length of up to about 18 carbon atoms, alkyl sulfates, alkyl sulfonates, and mixtures thereof.

27. A method according to claim 25, wherein the anionic surfactant comprises at least one of sodium dodecyl sulfate, alkyl polyoxyethylene sulfate, alkyl benzene sulfonate, alpha-olefin sulfonates, monoalkyl phosphates, acyl iosthionates, acyl glutamates, N-acyl sarcosinates, alkenyl succinates, and mixtures thereof.

28. A method according to claim 16, wherein the cleaning agent comprises an amphoteric surfactant comprising at least one of alkyl dimethyl amine oxides, alkyl carboxy betaines, alkyl sulfobetaines, amide-amino acid type amphoterics, and mixtures thereof.

29. A method according to claim 16, wherein the cleaning agent comprises a nonionic surfactant comprising at least one of polyoxyethylene alkyl ethers, polyethylene alkyl phenyl ethers, polyethylene fatty acid esters, sorbitan fatty acid esthers, polyethylene sorbitan fatty acid esters, sugar esters of fatty acids, alkyl polyglycosides, fatty acid diethanolamides, fatty acid monoglycerides, alkyl monoglycerol ethers, fatty acid polypropolene glycol esters, and mixtures thereof.

30. A method according to claim 16, wherein the cleaning agent comprises a cationic surfactant comprising at least one of ammonium salts, phosphonium salts, pyridinium salts, and mixtures thereof.

31. A method according to claim 16, wherein the mixture comprises a dispersant.

32. A method according to claim 16, wherein the mixture comprises an antifoaming agent.

33. A method according to claim 16, wherein the mixture comprises a chelating agent.

34. A method for cleaning a heat exchanger, the method comprising:

(a) applying a mixture of gas and liquid to a tube side of a shell-and-tube heat exchanger, the mixture comprising the gas and the liquid at a volumetric ratio of least about 50:1 when measured at 1 atmosphere and 0° C., and wherein at least a portion of the liquid is provided in the form of droplets and the liquid comprises at least one cleaning agent.

35. A method according to claim 34, wherein the volumetric ratio of the gas phase to the liquid phase is less than about 6,000:1 when measured at 1 atmosphere and 0° C.

36. A method according to claim 34, wherein the mixture is provided at a velocity of at least about 10 m/s.

37. A method according to claim 34, wherein the mixture is provided at a velocity of less than about 100 m/s.

38. A method according to claim 34, wherein the mixture is provided at a temperature above ambient temperature.

39. A method according to claim 34, wherein the cleaning agent comprises at least one of a surfactant, an oxidizing agent, an alcohol and a non-surfactant detergent.

40. A method according to claim 34, wherein the cleaning agent comprises an anionic surfactant.

41. A method according to claim 40, wherein the anionic surfactant comprises at least one of fatty acid soaps having an alkyl chain length of up to about 18 carbon atoms, alkyl sulfates, alkyl sulfonates, and mixtures thereof.

42. A method according to claim 40, wherein the anionic surfactant comprises at least one of sodium dodecyl sulfate, alkyl polyoxyethylene sulfate, alkyl benzene sulfonate, alpha-olefin sulfonates, monoalkyl phosphates, acyl iosthionates, acyl glutamates, N-acyl sarcosinates, alkenyl succinates, and mixtures thereof.

43. A method according to claim 34, wherein the cleaning agent comprises an amphoteric surfactant comprising at least one of alkyl dimethyl amine oxides, alkyl carboxy betaines, alkyl sulfobetaines, amide-amino acid type amphoterics, and mixtures thereof.

44. A method according to claim 34, wherein the cleaning agent comprises a nonionic surfactant comprising at least one of polyoxyethylene alkyl ethers, polyethylene alkyl phenyl ethers, polyethylene fatty acid esters, sorbitan fatty acid esthers, polyethylene sorbitan fatty acid esters, sugar esters of fatty acids, alkyl polyglycosides, fatty acid diethanolamides, fatty acid monoglycerides, alkyl monoglycerol ethers, fatty acid polypropolene glycol esters, and mixtures thereof.

45. A method according to claim 34, wherein the cleaning agent comprises a cationic surfactant comprising at least one of ammonium salts, phosphonium salts, pyridinium salts, and mixtures thereof.

46. A method according to claim 34, wherein the mixture comprises a dispersant.

47. A method according to claim 34, wherein the mixture comprises an antifoaming agent.

48. A method according to claim 34, wherein the mixture comprises a chelating agent.

\* \* \* \* \*